(12) United States Patent
Wang et al.

(10) Patent No.: US 11,175,228 B2
(45) Date of Patent: Nov. 16, 2021

(54) REACTIVE PEPTIDE LABELING

(71) Applicant: Promega Corporation, Madison, WI (US)

(72) Inventors: Hui Wang, Madison, WI (US); Nidhi Nath, Madison, WI (US); Rod Flemming, Madison, WI (US); Becky Godat, Madison, WI (US); Wenhui Zhou, Madison, WI (US); Virginia Kincaid, Madison, WI (US); Melanie Dart, Madison w, WI (US)

(*) Notice: Subject to any disclaimer, the term of this patent is extended or adjusted under 35 U.S.C. 154(b) by 104 days.

(21) Appl. No.: 16/698,143

(22) Filed: Nov. 27, 2019

(65) Prior Publication Data

US 2020/0166460 A1 May 28, 2020

Related U.S. Application Data

(60) Provisional application No. 62/772,448, filed on Nov. 28, 2018.

(51) Int. Cl.
*G01N 21/64* (2006.01)
*C07K 7/08* (2006.01)
(Continued)

(52) U.S. Cl.
CPC ....... *G01N 21/6428* (2013.01); *C07D 207/46* (2013.01); *C07K 1/13* (2013.01);
(Continued)

(58) Field of Classification Search
CPC ............ G01N 21/6428; G01N 33/542; G01N 33/582; G01N 2021/6439; C07D 207/46;
(Continued)

(56) References Cited

U.S. PATENT DOCUMENTS 8,557,970 B2   10/2013   Encell et al.
8,669,103 B2   3/2014    Encell et al.
(Continued)

FOREIGN PATENT DOCUMENTS

WO   WO 2010/127368   11/2010
WO   WO 2012/061530   5/2012
(Continued)

OTHER PUBLICATIONS

Hoang et al., "Quantitative Proteomics Employing Primary Amine Affinity Tags", Sep. 2003, J Biomol Tech, 14(3):216-223. (Year: 2003).*

(Continued)

*Primary Examiner* — Samuel P Siefke
*Assistant Examiner* — Henry H Nguyen
(74) *Attorney, Agent, or Firm* — Casimir Jones, S.C.; David W. Staple

(57) ABSTRACT

Provided herein are sulfo n-hydroxysuccimidyl ester (sulfo-SE) linked peptides, methods of synthesis thereof, and methods of using such peptides for labeling of biomolecules. In particular, peptides comprising non-alkyl group such as serine, threonine, cysteine, tyrosine, glutamic acid, and aspartic acid are stably modified (e.g., without autoreactivity) with a sulfo-SE group and used to label or otherwise modify biomolecules.

21 Claims, 16 Drawing Sheets

Specification includes a Sequence Listing.

(51) Int. Cl.
*G01N 33/542* (2006.01)
*C07K 1/13* (2006.01)
*C07K 14/00* (2006.01)
*C07D 207/46* (2006.01)
*C07K 16/24* (2006.01)

(52) U.S. Cl.
CPC .............. *C07K 7/08* (2013.01); *C07K 14/00* (2013.01); *G01N 33/542* (2013.01); *C07K 16/249* (2013.01); *C07K 2319/60* (2013.01); *G01N 2021/6439* (2013.01)

(58) Field of Classification Search
CPC . C07K 14/00; C07K 1/13; C07K 7/08; C07K 16/249; C07K 2319/60; C07K 16/248; C07K 14/70535; C07K 14/37; C07K 14/5412
See application file for complete search history.

(56) References Cited

U.S. PATENT DOCUMENTS

| | | |
|---|---|---|
| 9,056,885 B2 | 6/2015 | Kirkland et al. |
| 9,777,311 B2 | 10/2017 | Encell et al. |
| 9,797,889 B2 | 10/2017 | Dixon et al. |
| 9,797,890 B2 * | 10/2017 | Dixon ................. G01N 33/542 |
| 9,840,730 B2 | 12/2017 | Encell et al. |
| 9,869,670 B2 | 1/2018 | Dixon et al. |
| 9,951,373 B2 | 4/2018 | Encell et al. |
| 10,024,862 B2 | 7/2018 | Hitko et al. |
| 10,067,149 B2 | 9/2018 | Hitko et al. |
| 10,139,400 B2 | 11/2018 | Kirkland et al. |
| 10,215,751 B2 | 2/2019 | Kirkland et al. |
| 10,233,485 B2 | 3/2019 | Encell et al. |
| 10,633,690 B2 | 4/2020 | Encell et al. |
| 10,774,364 B2 | 9/2020 | Encell et al. |
| 2010/0221749 A1 * | 9/2010 | Clave ................. G01N 33/532 435/7.4 |
| 2019/0064192 A1 | 2/2019 | Hitko et al. |
| 2020/0248228 A1 | 8/2020 | Encell et al. |
| 2020/0270586 A1 | 8/2020 | Hall et al. |

FOREIGN PATENT DOCUMENTS

| | | |
|---|---|---|
| WO | WO 2013/078244 | 5/2013 |
| WO | WO 2014/093677 | 6/2014 |
| WO | WO 2014/151736 | 9/2014 |
| WO | WO 2019/241438 | 12/2019 |

OTHER PUBLICATIONS

Arai et al., "Demonstration of a Homogeneous Noncompetitive Immunoassay Based on Bioluminescence Resonance Energy Transfer", 2001, Analytical Biochemistry, 289, 77-91 (Year: 2001).*
Leavell et al, "Strategy for Selective Chemical Cross-Linking of Tyrosine and Lysine Residues", Nov. 2004, Journal of the American Society for Mass Spectrometry, 15, 11, p. 1604-1611 (Year: 2004).*
Stefan Kalkholf and Andrea Sinz, "Chances and pitfalls of chemical cross-linking with amine-reactive N-hydroxysuccinimide esters", 2008, Anal Bioanal Chem, 392:305-312 (Year: 2008).*
Blazeski et al., Engineered heart slices for electrophysiological and contractile studies. Biomaterials. Jul. 2015;55:119-28.
Blazeski et al., Functional Properties of Engineered Heart Slices Incorporating Human Induced Pluripotent Stem Cell-Derived Cardiomyocytes. Stem Cell Reports. May 14, 2019;12(5):982-995.
Dixon et al., NanoLuc Complementation Reporter Optimized for Accurate Measurement of Protein Interactions in Cells. ACS Chem Biol. Feb. 19, 2016;11(2):400-8.
Hudson et al., Engineered antibodies. Nat Med. Jan. 2003;9(1):129-34.
Isidro-Llobet et al., Amino acid-protecting groups. Chem Rev. Jun. 2009;109(6):2455-504.
Leavell et al., Strategy for selective chemical cross-linking of tyrosine and lysine residues. J Am Soc Mass Spectrom. Nov. 2004;15(11):1604-11.
Swaim et al., Unexpected products from the reaction of the synthetic cross-linker 3,3'-dithiobis(sulfosuccinimidyl propionate), DTSSP with peptides. J Am Soc Mass Spectrom. May 2004;15(5):736-49.
Zegzouti et al., Deciphering key cancer and inflammation signaling pathways with homogeneous bioluminescent cell-based kinase activity assys. Abstract 3446, AACR Annual Mtg, Chicago, IL 2018, 1 page.
International Search Report and Written Opinion for PCT/US2019/063652, dated Jun. 16, 2020, 21 pages.

* cited by examiner

Direct Immunoassay: Detection of mouse IgG

- Analyte: Mouse IgG
- Negative control: Human IgG
- Detection reagent
  - a-mouse-HT-LgBiT
  - a-mouse-SmBiT's (HaloTag vs SE-SmBiT)

➢ Conjugate made with sulfo-NHS-SmBiT (7649) gave higher signal and S/B

- Analyte: Fumonisin
- Negative control: No Fumonisin
- Detection reagent
  - a-Fumonisin-HT-LgBiT
  - Fumonisin-Biotin
  - SAv-SmBiT's (HaloTag vs 7649)

➢ 7649 offers significant improvement over HaloTag chemistry

FcRn Assay and new ligand

- Analyte: Human IgG
- Negative control: No Human IgG
- Detection reagent
  - Human IgG-LgBiT Tracer
  - FcRn-Biotin
  - Streptavidin-SmBiT's (HaloTag vs 7649)

- Wider assay window with 7649. This observation is consistent and has been verified in multiple assays.

REACTIVE PEPTIDE LABELING

CROSS-REFERENCE TO RELATED APPLICATION

The present application claims priority to U.S. Provisional Patent Application Ser. No. 62/772,448, filed Nov. 28, 2018, which is hereby incorporated by reference in its entireties.

FIELD

Provided herein are sulfo n-hydroxysuccimidyl ester (sulfo-SE) linked peptides, methods of synthesis thereof, and methods of using such peptides for labeling of biomolecules. In particular, peptides comprising non-alkyl group such as serine, threonine, tyrosine, glutamic acid, and aspartic acid are stably modified (e.g., without autoreactivity) with a sulfo-SE group and used to label or otherwise modify biomolecules.

BACKGROUND

The primary amine of lysine amino acids is a widely available reactive moiety on biomolecules and reacts readily with various agents, for example, an n-hydroxy succinimidyl ester (SE) group. A reaction between primary amines on biomolecules and SE containing fluorescent dyes, biotin, drugs, etc., have been used to label proteins, antibodies, etc., for use in a variety of applications. SE groups react with nucleophilic amino acid side chains, such as arginine, lysine, histidine, cysteine, serine, tyrosine, aspartic acid, glutamic acid, etc., therefore making SE containing peptides for subsequent peptide labeling of biomolecules has been avoided.

SUMMARY

Provided herein are sulfo n-hydroxysuccimidyl ester (sulfo-SE) linked peptides, methods of synthesis thereof, and methods of using such peptides for labeling of biomolecules. In particular, peptides comprising non-alkyl group such as serine, threonine, tyrosine, glutamic acid, and aspartic acid are stably modified (e.g., without autoreactivity) with a sulfo-SE group and used to label or otherwise modify biomolecules.

In some embodiments, provided herein are compositions comprising a peptide linked to a sulfo n-hydroxysuccinimidyl ester (sulfo-SE) group, wherein the peptide does not comprise a cysteine or lysine residue. In some embodiments, the sulfo-SE is linked to the N-terminus of the peptide. In some embodiments, the sulfo-SE is linked to the C-terminus of the peptide. In some embodiments, the sulfo-SE is linked to an amino acid sidechain of the peptide. In some embodiments, the peptide comprises at least one non-alkyl amino acid selected from serine, threonine, tyrosine, glutamic acid, arginine, histidine, tryptophan and aspartic acid. In some embodiments, the at least one reactive non-alkyl amino acid is a or tyrosine. In some embodiments, the at least one reactive nucleophilic amino acid is an arginine. In some embodiments, the sulfo-SE group is linked to the peptide by a non-peptide linker group. In some embodiments, the linker group comprises and alkyl or heteroalkyl chain. In some embodiments, the linker comprises one or more sidechain substituents. In some embodiments, the peptide is 4-50 amino acids in length. In some embodiments, the peptide is 8-20 amino acids in length. In some embodiments, the sulfo-SE is attached to the N-terminus of the peptide. In some embodiments, the sulfo-SE is attached to the N-terminus of the peptide via a linker group. In some embodiments, the peptides comprise a fluorophore or chromophore conjugate. In some embodiments, the peptide is a component of a biomolecular complex. In some embodiments, the peptide is a component of a biomolecular complex. In some embodiments, the peptide comprises 5 or fewer substitutions relative to SEQ ID NO: 10 (SmBit). In some embodiments, one or more lysines are replaced with an arginine. In some embodiments, one or more lysines of SEQ ID NO: 10 are replaced with an arginine. In some embodiments, the peptide comprises Pep691 (SEQ ID NO: 23). In some embodiments, the peptide comprises SmBiT (SEQ ID NO: 10). In some embodiments, the peptide is conjugated to a fluorophore. In some embodiments, the peptide comprises fluorophore conjugated to an arginine. In some embodiments, the peptide comprises fluorophore conjugated to SEQ ID NO: 23. In some embodiments, the peptide comprises fluorophore conjugated to SEQ ID NO: 10.

In some embodiments, provided herein are methods of labeling a biomolecule with a peptide comprising contacting the biomolecule with a sulfo-SE linked peptide described herein, under conditions such that the sulfo-SE group reacts with an amine on the biomolecule. In some embodiments, a peptide composition contacts the biomolecule under conditions such that the sulfo-SE group reacts with amine on the biomolecule. In some embodiments, the amine is a primary amine. In some embodiments, the biomolecule is selected from the group consisting of an antigen, an antibody, an antibody fragment, a nanobody, a darpin, a non-antibody protein, a receptor, a ligand, a toxin, a cytokine, a nucleic acid, a nucleoprotein complex, a peptide, an amino acid, a sugar, a drug, and streptavidin.

In some embodiments, provided herein are methods of labeling a peptide with a sulfo-SE moiety comprising contacting the peptide with a sulfo-NHS compound under conditions such that the hydroxy of the sulfo-NHS compound reacts with the terminal amine of the peptide, wherein the peptide does not comprise an cysteine or lysine residue. In some embodiments, the peptide comprises at least one reactive nucleophilic amino acid.

In some embodiments, provided herein are compositions comprising a biomolecule labeled with a sulfo-SE linked peptide described herein.

In some embodiments, provided herein are methods comprising contacting comprising a biomolecule labeled with a sulfo-SE linked peptide described herein with an analyte. In some embodiments, the analyte is selected from the group consisting of an antigen, an antibody, an antibody fragment, a nanobody, a darpin, a non-antibody protein, a receptor, a ligand, a toxin, a cytokine, a nucleic acid, a nucleoprotein complex, a peptide, an amino acid, a sugar, a drug, and streptavidin. In some embodiments, the analyte is linked to a complementary polypeptide capable of forming a bioluminescent complex with the peptide on the biomolecule. In some embodiments, methods further comprise contacting the bioluminescent complex with a substrate for the bioluminescent complex and detecting luminescence.

In some embodiments, provided herein are compositions comprising an analyte labeled with a sulfo-SE linked peptide described herein.

In some embodiments, provided herein are methods comprising contacting an analyte labeled with a sulfo-SE linked peptide described herein with a biomolecule. In some embodiments, the biomolecule is linked to a complementary polypeptide capable of forming a bioluminescent complex with the peptide on the analyte. In some embodiments, methods further comprise contacting the bioluminescent complex with a substrate for the bioluminescent complex and detecting luminescence, fluorescence, and/or BRET.

In some embodiments, provided herein are compositions comprising an analyte labeled with a first sulfo-SE linked peptide described herein and a biomolecule labelled with a second sulfo-SE linked peptide described herein, wherein the first and second peptides are capable of forming a bioluminescent complex in the presence of a complementary polypeptide. In some embodiments, methods comprise contacting the analyte and biomolecule with the complementary polypeptide and forming the bioluminescent complex. In some embodiments, methods further comprise contacting the bioluminescent complex with a substrate for the bioluminescent complex and detecting luminescence.

In some methods herein, one or more of the peptides is a fluorophore or chromophore-conjugated peptide. These methods further comprise detecting fluorescence/light and/or BRET from a bioluminescent complex to the fluorophore or chromophore. In some embodiments, the number of labeling per biomolecule is calculated by the number of fluorophore or chromophore molecules per biomolecule. In some embodiments, the fluorophore molecule is a FAM, TAMRA, ROX, silo-rhodamine, BODIPY, TOM, Dyomics dye, or a carbon-rhodamine, but not limited to those fluorophores.

In some embodiments, provided herein are methods comprising (a) forming a bioluminescent complex of a SEQ ID NO: 10 (SmBiT) labeled-analyte biomolecule and the LgBiT-labeled analyte biomolecule specific antibody; (b) contacting the bioluminescent complex with the analyte; (c) contacting the bioluminescent complex with a substrate for the bioluminescent complex; and (d) detecting light output from the bioluminescent complex.

In some embodiments, provided herein are methods comprising (a) contacting an analyte with a SEQ ID NO: 10 (SmBiT) labeled-analyte specific antibody and a LgBiT-labeled analyte-specific antibody and forming a bioluminescent complex; (b) contacting the bioluminescent complex with a substrate for the bioluminescent complex; and (c) detecting light output from the bioluminescent complex.

In some embodiments, provided herein are methods comprising (a) contacting an analyte with a SEQ ID NO: 10 (SmBiT) labeled-analyte specific antibody, a SEQ ID NO: 11 (HiBiT)-labeled analyte-specific antibody, and a polypeptide copable for forming a bioluminescent complex with HiBiT and SmBiT; (b) contacting the bioluminescent complex with a substrate for the bioluminescent complex; and (c) detecting light output from the bioluminescent complex.

In some embodiments, provided herein are methods comprising: (a) contacting an analyte with a SEQ ID NO: 10 (SmBiT) labeled-analyte specific antibody, a SEQ ID NO: 11 (HiBiT)-labeled analyte-specific antibody, and a polypeptide capable for forming a bioluminescent complex with HiBiT and SmBiT; (b) contacting the bioluminescent complex with a substrate for the bioluminescent complex; (c) detecting light output from the bioluminescent complex.

In some embodiments, provided herein are methods comprising contacting an analyte with a biomolecule labeled with a sulfo-SE linked peptide described herein. In some embodiments, the analyte is selected from the group consisting of an antigen, an antibody, a non-antibody protein, a receptor, a ligand, a toxin, a cytokine, a nucleic acid, a peptide, an amino acid, a sugar, a drug, a nucleoprotein complex, biotin, and streptavidin. In some embodiments, the analyte biomolecule is labeled with SEQ ID NO: 10 (SmBiT).

In some embodiments, methods comprise: (a) forming a bioluminescent complex from a SEQ ID NO: 10 (SmBiT) labeled-analyte biomolecule and a LgBiT-labeled analyte biomolecule specific antibody; (b) contacting the bioluminescent complex with the analyte; (c) contacting the bioluminescent complex with a substrate for the bioluminescent complex; and (d) detecting light output from the bioluminescent complex.

In some embodiments, methods comprise: (a) forming a bioluminescent complex from SEQ ID NO: 10 (SmBiT) labeled- and LgBiT-labeled analyte specific antibodies; (b) contacting the bioluminescent complex with the analyte; (c) contacting the bioluminescent complex with a substrate for the bioluminescent complex; and (d) detecting light output from the bioluminescent complex.

In some embodiments, methods comprise: (a) contacting an analyte with SEQ ID NO: 10 (SmBiT)-labeled antibodies or receptors and SEQ ID NO: 11 (HiBiT)-labeled antibodies or receptors; (b) contacting the analyte with LgBiT to form a bioluminescent complex; (c) contacting the bioluminescent complex with a substrate for the bioluminescent complex; and (d) detecting light output from the bioluminescent complex.

In some embodiments, methods comprise: (a) contacting SmBiT- or HiBiT-labeled-analyte biomolecule with a HiBiT- or SmBiT-labeled analyte biomolecule specific antibody; (b) contacting with LgBiT to form a bioluminescent complex; (c) contacting with the analyte; (d) contacting the bioluminescent complex with a substrate for the bioluminescent complex; and (e) detecting light output from the bioluminescent complex. In some embodiments, the peptide is a fluorophore or chromophore-conjugated peptide. In some embodiments, the number of labeling per biomolecule is calculated by the number of fluorophore or chromophore molecules per biomolecule. In some embodiments, the fluorophore molecule is a FAM, TAMRA, ROX, silo-rhodamine, BODIPY, TOM, Dyomics dye, or a carbon-rhodamine, but not limited to those fluorophores.

In some embodiments, methods comprise: (a) forming a bioluminescent complex from a fluorophore-conjugated SEQ ID NO: 10 (SmBiT) labeled-analyte biomolecule and a LgBiT-labeled analyte biomolecule specific antibody; (b) contacting the bioluminescent complex with the analyte; (c) contacting the bioluminescent complex with a substrate for the bioluminescent complex; and (d) detecting light output from the bioluminescent complex.

In some embodiments, methods comprise: (a) contacting an analyte with both a fluorophore-conjugated SEQ ID NO: 10 (SmBiT) labeled- and LgBiT-labeled analyte specific antibodies, forming a bioluminescent complex; (b) contacting the bioluminescent complex with a substrate for the bioluminescent complex; (c) detecting light output from the bioluminescent complex.

In some embodiments, methods comprise: (a) one of SEQ ID NO: 10 (SmBiT) and SEQ ID NO: 11 (HiBiT)-peptides is the fluorophore-conjugated peptide; (b) the analyte contacts SEQ ID NO: 10 (SmBiT) and SEQ ID NO: 11 (HiBiT)-labeled antibodies, or receptors, or combination, wherein one of the peptides is a fluorophore-conjugated peptide; (b) contacting with LgBiT to form a bioluminescent complex; (c) contacting the bioluminescent complex with a substrate for the bioluminescent complex; and (d) detecting light output from the bioluminescent complex.

In some embodiments, provided herein are methods wherein the analyte biomolecule or analyte specific antibody is labeled with fluorophore-conjugated SEQ ID NO: 10 (SmBiT) or SEQ ID NO: 11 (HiBiT), wherein (a) SEQ ID NO: 10 (SmBiT) or SEQ ID NO: 11 HiBiT.labeled-analyte biomolecule contacts the SEQ ID NO: 11 (HiBiT) or SEQ ID NO: 10 (SmBiT)-labeled analyte biomolecule specific antibody, wherein one of the peptides is the fluorophore-conjugated peptide; (b) contacting with LgBiT to form a bioluminescent complex; (c) contacting with the analyte; (d) contacting the bioluminescent complex with a substrate for the bioluminescent complex; and (e) detecting light output from the bioluminescent complex.

DEFINITIONS

Figure 1A:
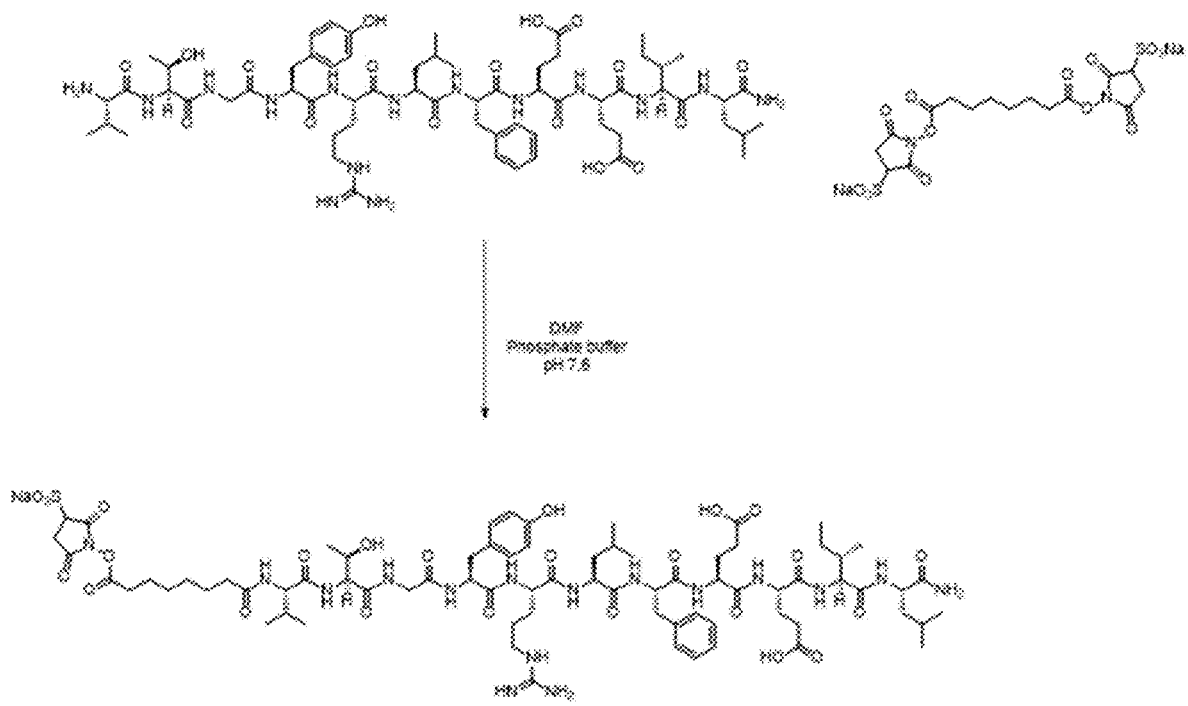
FIGS. 1A-B. Synthetic schemes for attaching a generic sulfo-SE group to a generic peptide: (A) the target peptide was reacted directly with bis-sulfo-SE: one of the sulfo-SE reacts with free amine on the N-terminus, C-terminus or side chain while leaving the other sulfo-SE intact); (B) the protected peptide on resin is first coupled with bis-Sulfo SE at either N-terminus or side chain, and the resulting peptide was then cleaved off resin in trifluoroacetic acid.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an", and "the" include plural reference unless the context clearly dictates otherwise. Thus, for example, reference to "a peptide" is a reference to one or more peptides and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "substantially" means that the recited characteristic, parameter, and/or value need not be achieved exactly, but that deviations or variations, including for example, tolerances, measurement error, measurement accuracy limitations and other factors known to skill in the art, may occur in amounts that do not preclude the effect the characteristic was intended to provide. A characteristic or feature that is substantially absent (e.g., substantially non-luminescent) may be one that is within the noise, beneath background, below the detection capabilities of the assay being used, or a small fraction (e.g., <1%, <0.1%, <0.01%, <0.001%, <0.00001%, <0.000001%, <0.0000001%) of the significant characteristic (e.g., luminescent intensity of a bioluminescent protein or bioluminescent complex).

As used herein, the term "sulfo n-hydroxysuccinimidyl ester" ("sulfo-SE") refers to a moiety on a chemical or biomolecule having the chemical structure:

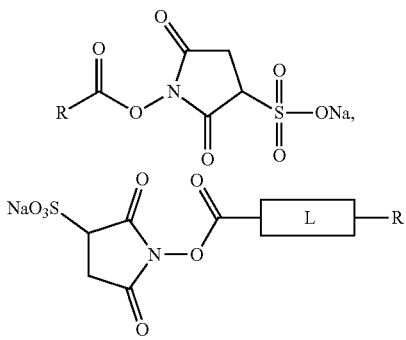

wherein R is the chemical or biomolecule (e.g., peptide) and L is any suitable linker (as described herein) connecting the sulfo-SE group to the chemical or biomolecule (e.g., peptide).

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, pentafluorophenylalanine ("Z"), azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), citruiline, halo-substituted tyrosine, and homoArginine ("hArg"). Unnatural reactive amino acids are described in, for example, Boutureira, O. and G. J. Bernardes (2015) "Advances in chemical protein modification." Chem Rev 115(5): 2174-2195; herein incorporated by reference in its entirety.

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone. Amino acid analogs may comprise amino acids with various protecting groups (Isidro-Llobet, A., et al. (2009). "Amino Acid-Protecting Groups." Chemical Reviews 109(6): 2455-2504; herein incorporated by reference in its entirety).

As used herein, unless otherwise specified, the terms "peptide" and "polypeptide" refer to polymer compounds of two or more amino acids joined through the main chain by peptide amide bonds (—C(O)NH—). The term "peptide" typically refers to short amino acid polymers (e.g., chains having fewer than 50 amino acids), whereas the term "polypeptide" typically refers to longer amino acid polymers (e.g., chains having more than 50 amino acids).

As used herein, terms "peptidomimetic" and "peptide mimetic" refer to peptide-like or polypeptide-like molecules that emulate a sequence derived from a protein or peptide. A peptidomimetic may contain amino acids analogs, peptoid amino acids, and/or non-amino acid components either exclusively or in combination with amino acids (e.g., natural or non-natural amino acids). Examples of peptidomimetics include chemically modified peptides/polypeptides, peptoids (side chains are appended to the nitrogen atom of the peptide backbone rather than to the α-carbons), β-peptides (amino group bonded to the β carbon rather than the α carbon), etc.

As used herein, the term "peptoid" refers to a class of peptidomimetics where the side chains are functionalized on the nitrogen atom of the peptide backbone rather than to the α-carbon.

As used herein, the term "artificial" refers to compositions and systems that are designed or prepared by man and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W));

proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any peptide/polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum, and the like. Sample may also refer to cell lysates or purified forms of the enzymes, peptides, and/or polypeptides described herein. Cell lysates may include cells that have been lysed with a lysing agent or lysates such as rabbit reticulocyte or wheat germ lysates. Sample may also include cell-free expression systems. Environmental samples include environmental material such as surface matter, soil, water, crystals, and industrial samples. Such examples are not however to be construed as limiting the sample types applicable to the present invention.

As used herein, the term "physiological conditions" encompasses any conditions compatible with living cells, e.g., predominantly aqueous conditions of a temperature, pH, salinity, chemical makeup, etc. that are compatible with living cells.

As used herein, the terms "conjugated" and "conjugation" refer to the covalent attachment of two molecular entities (e.g., post-synthesis and/or during synthetic production). The attachment of a peptide or small molecule tag to a protein or small molecule, chemically (e.g., "chemically" conjugated) or enzymatically, is an example of conjugation. The reaction of a SE-peptide with an amine on a biomolecule results in conjugation of the peptide with the biomolecule.

The term "binding moiety" refers to a domain that specifically binds an antigen or epitope independently of a different epitope or antigen binding domain. A binding moiety may be an antibody, antibody fragment, a receptor domain that binds a target ligand, proteins that bind to immunoglobulins (e.g., protein A, protein G, protein A/G, protein L, protein M), a binding domain of a proteins that bind to immunoglobulins (e.g., protein A, protein G, protein A/G, protein L, protein M), oligonucleotide probe, peptide nucleic acid, DARPin, aptamer, affimer, a purified protein (either the analyte itself or a protein that binds to the analyte), and analyte binding domain(s) of proteins etc. Table A provides a list of exemplary binding moieties that could be used singly or in various combinations in methods, systems, and assays (e.g., immunoassays) herein.

TABLE A

| Exemplary binding moieties |
|---|
| Protein A |
| Ig Binding domain of protein A |
| Protein G |
| Ig Binding domain of protein G |
| Protein L |
| Ig Binding domain of protein L |
| Protein M |
| Ig Binding domain of protein M |
| polyclonal antibody against analyte X |
| monoclonal antibody |
| recombinant antibody |
| scFv |
| variable light chain ($V_L$) of antibody (monoclonal, |

TABLE A-continued

Exemplary binding moieties recombinant, polyclonal) recognizing target
analyte X
protein (e.g. receptor) binding domain that binds
to analyte X
(Fab) fragment
Fab' fragment
Fv fragment
F(ab')2 fragment
oligonucleotide probe
DARPins and other synthetic binding scaffolds (ex:
Bicycles)
peptide nucleic acid
aptamer
affinner As used herein, the term "antibody" refers to a whole antibody molecule or a fragment thereof (e.g., fragments such as Fab, Fab', and F(ab')$_2$, variable light chain, variable heavy chain, Fv, it may be a polyclonal or monoclonal or recombinant antibody, a chimeric antibody, a humanized antibody, a human antibody, etc. As used herein, when an antibody or other entity "specifically recognizes" or "specifically binds" an antigen or epitope, it preferentially recognizes the antigen in a complex mixture of proteins and/or macromolecules and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ M$^{-1}$ (e.g., >$10^7$ M$^{-1}$, >$10^8$ M$^{-1}$, >$10^9$ M$^{-1}$, >$10^{10}$ M$^{-1}$, >$10^{11}$ M$^{-1}$, >$10^{12}$ M$^{-1}$, >$10^{13}$ M$^{-1}$, etc.). In certain such embodiments, an antibody is capable of binding different antigens so long as the different antigens comprise that particular epitope. In certain instances, for example, homologous proteins from different species may comprise the same epitope.

As used herein, the term "antibody fragment" refers to a portion of a full-length antibody, including at least a portion of the antigen binding region or a variable region. Antibody fragments include, but are not limited to, Fab, Fab', F(ab')$_2$, Fv, scFv, Fd, variable light chain, variable heavy chain, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis. For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises an additional constant region extending between the $C_{H1}$ and $C_{H2}$ domains. An interchain disulfide bond can be formed between two heavy chains of a Fab' fragment to form a "F(ab')$_2$" molecule. An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen. Other antibody fragments will be understood by skilled artisans.

As used herein, the term "peptide tag" refers to a peptide that may be attached (e.g., post-synthesis or during synthetic production) or fused to another entity (e.g., a biomolecule). In typical embodiments herein, a peptide tag displays (is linked to) a sulfo-SE group (e.g., for conjugation of the peptide to a biomolecule). In certain embodiments herein, a peptide tag is capable of forming a bioluminescent complex with (i) a polypeptide and/or (ii) another peptide tag and a polypeptide, under appropriate conditions.

As used herein, the term "biomolecule" or "biological molecule" is refer to molecules and ions that are present in organisms and are essential to a biological process(es) such as cell division, morphogenesis, or development. [1] Biomolecules include large macromolecules (or polyanions) such as proteins, carbohydrates, lipids, and nucleic acids as well as small molecules such as primary metabolites, secondary metabolites, and natural products. A more general name for this class of material is biological materials. Biomolecules are usually endogenous, but may also be exogenous. For example, pharmaceutical drugs may be natural products or semisynthetic (biopharmaceuticals), or they may be totally synthetic.

As used herein, the term "bioluminescence" refers to production and emission of light by a chemical reaction catalyzed by, or enabled by, an enzyme, protein, protein complex, or other biomolecule (e.g., bioluminescent complex). In typical embodiments, a substrate for a bioluminescent entity (e.g., bioluminescent protein or bioluminescent complex) is converted into an unstable form by the bioluminescent entity; the substrate subsequently emits light. As used herein, the term "non-luminescent" refers to an entity (e.g., peptide, polypeptide, complex, protein, etc.) that exhibits the characteristic of not emitting a detectable amount of light in the visible spectrum (e.g., in the presence of a substrate). For example, an entity may be referred to as non-luminescent if it does not exhibit detectable luminescence in a given assay. As used herein, the term "non-luminescent" is synonymous with the term "substantially non-luminescent. In some embodiments, an entity is considered "non-luminescent" if any light emission is sufficiently minimal so as not to create interfering background for a particular assay.

As used herein, the terms "non-luminescent peptide" and "non-luminescent polypeptide" refer to peptides and polypeptides that exhibit substantially no luminescence (e.g., in the presence of a substrate), or an amount that is beneath the noise (e.g., 100-fold, 200-fold, 500-fold, $1\times10^3$-fold, $1\times10^4$-fold, $1\times10^5$-fold, $1\times10^6$-fold, $1\times10^7$-fold, etc.), when compared to a significant signal (e.g., a bioluminescent complex) under standard conditions (e.g., physiological conditions, assay conditions, etc.) and with typical instrumentation (e.g., luminometer, etc.). In some embodiments, such non-luminescent peptides and polypeptides assemble, according to the criteria described herein, to form a bioluminescent complex.

As used herein, the term "an Oplophorus luciferase" ("an OgLuc") refers to a luminescent polypeptide having significant sequence identity, structural conservation, and/or the functional activity of the luciferase produce by and derived from the deep-sea shrimp *Oplophorus gracilirostris*. In particular, an OgLuc polypeptide refers to a luminescent polypeptide having significant sequence identity, structural conservation, and/or the functional activity of the mature 19 kDa subunit of the Oplophorus luciferase protein complex (e.g., without a signal sequence) such as SEQ ID NOs: 1 (WT OgLuc) and 3 (NanoLuc), which comprises 10 β strands (β1, β2, β3, β4, β5, β6, β7, β8, β9, β10) and utilize substrates such as coelenterazine or a coelenterazine derivative or analog to produce luminescence.

As used herein the term "complementary" refers to the characteristic of two or more structural elements (e.g., peptide, polypeptide, nucleic acid, small molecule, etc.) of being able to hybridize, dimerize, or otherwise form a complex with each other. For example, a "complementary peptide and polypeptide" are capable of coming together to form a complex. Complementary elements may require assistance (facilitation) to form a complex (e.g., from interaction elements), for example, to place the elements in the proper conformation for complementarity, to place the elements in the proper proximity for complementarity, to co-localize complementary elements, to lower interaction energy for complementary, to overcome insufficient affinity for one another, etc.

As used herein, the term "complex" refers to an assemblage or aggregate of molecules (e.g., peptides, polypeptides, etc.) in direct and/or indirect contact with one another. In one aspect, "contact," or more particularly, "direct contact" means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules (e.g., peptides and polypeptide) is formed under assay conditions such that the complex is thermodynamically favored (e.g., compared to a non-aggregated, or non-complexed, state of its component molecules). As used herein the term "complex," unless described as otherwise, refers to the assemblage of two or more molecules (e.g., peptides, polypeptides or a combination thereof).

As used herein, the term "β9-like peptide" refers to a peptide (or peptide tag) comprising significant sequence identity, structural conservation, and/or the functional activity of the β (beta) 9 strand of an OgLuc polypeptide. In particular, a β9-like peptide is a peptide capable of structurally complementing an OgLuc polypeptide lacking a β9 strand resulting in enhanced luminescence of the complex compared to the OgLuc polypeptide in the absence of the β9-like peptide. Other "βX-like peptides" may be similarly named (e.g., β1-like, β2-like, β3-like, β4-like, β5-like, β6-like, β7-like, β8-like, β9-like). In some embodiments, a β9-like peptide is linked to a sulfo-SE group for conjugation to a biomolecule.

As used herein, the term "β10-like peptide" refers to a peptide (or peptide tag) comprising significant sequence identity, structural conservation, and/or the functional activity of the β(beta) 10 strand of an OgLuc polypeptide. In particular, a β10-like peptide is a peptide capable of structurally complementing an OgLuc polypeptide lacking a β10 strand resulting in enhanced luminescence of the complex compared to the OgLuc polypeptide in the absence of the β10-like peptide. Other "βX-like peptides" may be similarly named (e.g., β1-like, β2-like, β3-like, β4-like, β5-like, β6-like, β7-like, β8-like, β9-like). In some embodiments, a β10-like peptide is linked to a sulfo-SE group for conjugation to a biomolecule.

As used herein, the term "$\beta_{1-8}$-like polypeptide" refers to a polypeptide bearing sequence and structural similarity to β(beta) strands 1-8 of an OgLuc polypeptide, but lacking β(beta) strands 9 and 10. Other "$\beta_{Y-Z}$-like polypeptides" may be similarly named (e.g., $\beta_{1-4}$-like polypeptide, $\beta_{2-8}$-like polypeptide, $\beta_{5-10}$-like polypeptide, etc.).

As used herein, the term "NANOLUC" refers to an artificial luciferase or bioluminescent polypeptide produced commercially by the Promega Corporation and corresponding to SEQ ID NO: 3.

As used herein, the term "LgBiT" refers to a polypeptide corresponding to $\beta_{1-9}$-like polypeptide that finds use in, for example, binary complementation to form a bioluminescent complex and corresponds to SEQ ID NO: 11.

As used herein, the term "SmBiT" refers to a peptide corresponding to $\beta_{10}$-like peptide that finds use in, for example, binary complementation to form a bioluminescent complex, but has low affinity for LgBiT (e.g., requires facilitation for complex formation) and corresponds to SEQ ID NO: 13. In some embodiments, SmBit, or variants thereof, is linked to a sulfo-SE, for conjugation to a biomolecule.

As used herein, the term "HiBiT" refers to a peptide corresponding to $\beta_{10}$-like peptide that finds use in, for example, binary complementation to form a bioluminescent complex, but has low affinity for LgBiT (e.g., requires facilitation for complex formation). An exemplary HiBiT peptide corresponds to SEQ ID NO: 15. HiBiT is has the same sequence as "SmHiTrip10" (SEQ ID NO: 11) and "pep86," terms which may be used interchangeably (also SmTrip10 pep86, etc.). In some embodiments, HiBiT variants lacking cysteine and lysine residues are linked to a sulfo-SE for conjugation to a biomolecule.

As used herein, the term "LgTrip" refers to a polypeptide corresponding to $\beta_{1-8}$-like polypeptide. An exemplary LgTrip corresponds to SEQ ID NO: 17 and finds use in, for example, tripartite complementation with $\beta_9$-like and $\beta_{10}$-like peptides to form a bioluminescent complex, or binary complementation, with a $\beta_{9-10}$-like dipeptide to form a bioluminescent complex. LgTrip variants include: LgTrip 2098 (w/His tag: SEQ ID NO: 31; w/o His tag: SEQ ID NO: 304) and LgTrip 3546 (w/His tag: SEQ ID NO: 51; w/o His tag: SEQ ID NO: 302).

As used herein, the term "SmTrip10" refers to a peptide corresponding to $\beta_{10}$-like peptide that finds use in, for example, tripartite complementation to form a bioluminescent complex. In some embodiments, SmTrip10, or variants thereof, is linked to a sulfo-SE, for conjugation to a biomolecule.

As used herein, the term "SmTrip9" refers to a peptide corresponding to $\beta_9$-like peptide that finds use in, for example, tripartite complementation to form a bioluminescent complex. In some embodiments, SmTrip9, or variants thereof, is linked to a sulfo-SE, for conjugation to a biomolecule.

Various peptide and polypeptide sequences that find use in certain embodiments herein are described in U.S. Pat. No. 9,797,889 (herein incorporated by reference in its entirety) and Intl. App. No. PCT/US19/36844 (herein incorporated by reference in its entirety).

DETAILED DESCRIPTION

Provided herein are sulfo n-hydroxysuccimidyl ester (sulfo-SE) linked peptides, methods of synthesis thereof, and methods of using such peptides for labeling of biomolecules. In particular, peptides comprising a non-alkyl group(s) such as serine, threonine, arginine, tyrosine, glutamic acid, and aspartic acid are stably modified (e.g., without autoreactivity) with a sulfo-SE group and used to label or otherwise modify biomolecules.

Synthesizing sulfo-SE peptides (e.g., peptides displaying sulfo-SE groups) is not trivial due to the high potential for autoreactivity of SE groups with the peptides to which they are attached. For example, the presence of amino acids with accessible nucleophilic side chains (e.g., arginine, lysine, histidine, cysteine, serine, tyrosine, etc.) on a peptide has been understood by the field to result in potential autoreactivity of the SE-group with such a residue. As such, peptide attachment to biomolecules through SE reaction with exposed amines on biomolecules has not been pursued. However, experiments conducted during development of embodiments herein have demonstrated the successful attachment of N-hydroxysulfosuccinimide (sulfo-NHS) to a peptide lacking lysine and cysteine residues (but containing other nucleophilic residues) resulting in the formation of a sulfo n-hydroxysuccinimidyl ester (sulfo-SE) on the N-terminus of the peptide without subsequence autoreactivity of the sulfo-SE group with the peptide. The sulfo-SE labeled peptide was subsequently used to peptide-label biomolecules (e.g., streptavidin, antibodies, etc.) via reaction of the sulfo-SE group with primary amines on the biomolecules. These experiments demonstrate that stable sulfo-SE peptides can be generated by the reaction of sulfo-NHS with peptides (e.g., peptides lacking lysine and cysteine amino acids) to produce useful reagents for the peptide labeling of biomolecules.

Figure 1B:
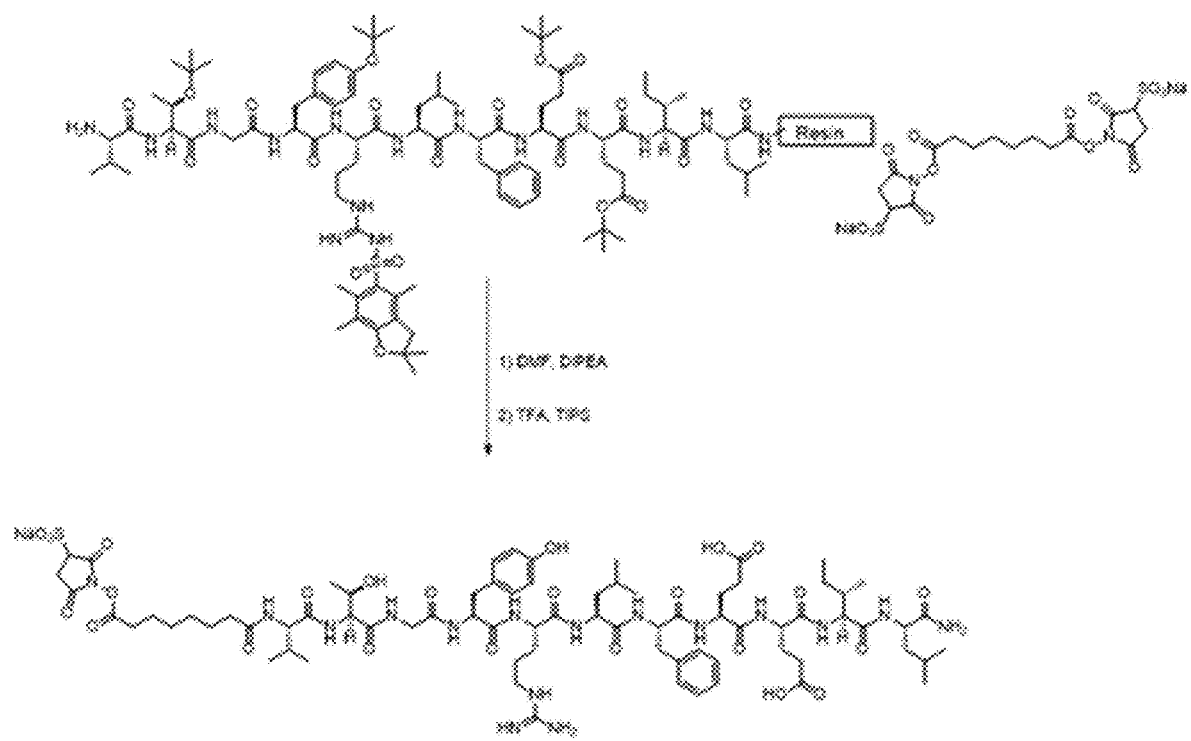

In some embodiments, provided herein are methods for the synthesis of sulfo-SE peptides (FIG. 1). In some embodiments, a peptide is combined with bis-sulfo-SE (e.g., under appropriate reaction conditions (e.g., in PBS buffer, pH 7.6)) to produce a sulfo-SE-peptide (e.g., sulfo-SE/peptide conjugate). In some embodiments, the bis-sulfo-SE reacts with the N-terminal amine of the peptide on resin to result in an end-labeled peptide on resin and it was cleaved off resin with trifluoroacetic acid. Experiments conducted during development of embodiments herein demonstrate that in the absence of lysine and cysteine residues in the peptide, the sulfo-SE group will not autoreact with the side chains of the peptide.

In some embodiments, a suitable peptide for addition to an N-terminal sulfo-SE label is, for example, 4 to 50 amino acids in length (e.g., 4, 5, 6, 7, 8, 9, 10, 12, 14, 16, 18, 20, 25, 30, 35, 40, 45, 50, or ranges therebetween). In some embodiments, the peptide lacks cysteine residues. In some embodiments, the peptide lacks lysine residues. In some embodiments, the peptide comprises one or more (e.g., 1, 2, 3, 4, 5, 6, 7, 8, 9, 10, or more, or ranges therebetween) amino acids with a non-alkyl group such as histidine, arginine, serine, tyrosine, aspartic acid, glutamic acid. In some embodiments, the peptide comprises one or more (e.g., 1, 2, 3, 4, 5, 6, 7, 8, 9, 10, or more, or ranges therebetween) tyrosine, arginine, and/or glutamic acid amino acids.

In some embodiments, provided herein are compositions for attaching a sulfo-SE moiety to a suitable peptide. In some embodiments, a bis-sulfo-SE compound is provided. In some embodiments, provided herein are compounds having a chemical structure of:

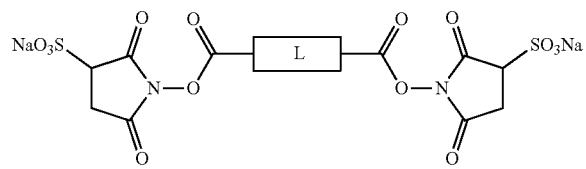

wherein L is any suitable linker (as described herein). In some embodiments, L is selected from a straight alkyl chain (e.g., 1-20 carbons), a branched alkyl chain (e.g., 1-20 carbons), a straight heteroalkyl (e.g., O, N, or S atoms within the alkyl), a branched heteroalkyl, a substituted alkyl (e.g., suitable functional groups along the alkyl chain), substituted heteroalkyl, etc. In some embodiments, the linker comprises a linear or branched, cyclic or heterocyclic, saturated or unsaturated, structure having 1-20 nonhydrogen atoms (e.g., C, N, P, O and S) and is composed of any combination of alkyl, ether, thioether, imine, carboxylic, amine, ester, carboxamide, sulfonamide, hydrazide bonds, carbamate, and aromatic or heteroaromatic bonds. In some embodiments, linkers are longer than 20 nonhydrogen atoms (e.g. 21 non-hydrogen atoms, 25 non-hydrogen atoms, 30 non-hydrogen atoms, 40 non-hydrogen atoms, 50 non-hydrogen atoms, 100 non-hydrogen atoms, etc.) In some embodiments, the linker comprises 1-50 non-hydrogen atoms (in addition to hydrogen atoms) selected from the group of C, N, P, O and S (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 non-hydrogen atoms). In some embodiments, a linker comprises a combination of $CH_2$, $(CH_2)_2O$, and carbamate groups. For example, a linked may comprise —OC(O)$(CH_2)_6$C(O)—, or any other suitable combination of the functional groups described herein.

In some embodiments, provided herein are reactants or a reaction mix comprising sulfo-NHS (with or without an R linker group) and a suitable peptide for reaction therewith (e.g., a peptide lacking lysine and cysteine residues, but optionally containing one or more other reactive nucleophilic amino acids).

In some embodiments, provided herein are sulfo-SE peptides. In some embodiments, peptides display a sulfo-SE group on the N-terminus of the peptide. In some embodiments, peptide display a sulfo-SE group on the C-terminus of the peptide. In some embodiments, peptide display a sulfo-SE group on the side chain of the peptide. In some embodiments, the peptide lacks lysine and cysteine residues, but optionally containing one or more other reactive nucleophilic amino acids. In some embodiments, sulfo-SE peptides are universal reagents for conjugating peptides to targets of interest (e.g., biomolecules).

In some embodiments, provided herein are methods for the labeling a biomolecule with a peptide tag. In some embodiments, the biomolecule comprises any suitable protein, polynucleotide, polypeptide, biomolecular complex, natural product, synthetic macromolecule, etc., that displays one or more amine groups (e.g., primary amine). In some embodiments, one or more amine groups are displayed on the surface and/or a solvent accessible region of the biomolecule. In some embodiments, the biomolecule comprises 1-100 (e.g., 1, 2, 3, 4, 5, 6, 7, 8, 9, 10, 15, 20, 25, 30, 40, 50, 60, 70, 80, 90, 100, or ranges therebetween) amine (e.g., primary amine) groups (e.g., accessible amine groups). In some embodiments, a biomolecule for targeting with a sulfo-SE peptide is a protein, enzyme, receptor, antibody, antibody fragment, polypeptide, toxin, cytokine, polynucleotides, drugs, small molecules, ligand, inhibitors, biomolecular complex (e.g., comprising one or more components selected from protein(s), polynucleotides (e.g., DNA, RNA), carbohydrates, lipids, small molecules, etc.), primary metabolites, secondary metabolites, and natural products, exogenous biomolecules, such as, pharmaceutical drugs, etc.

Figure 2:
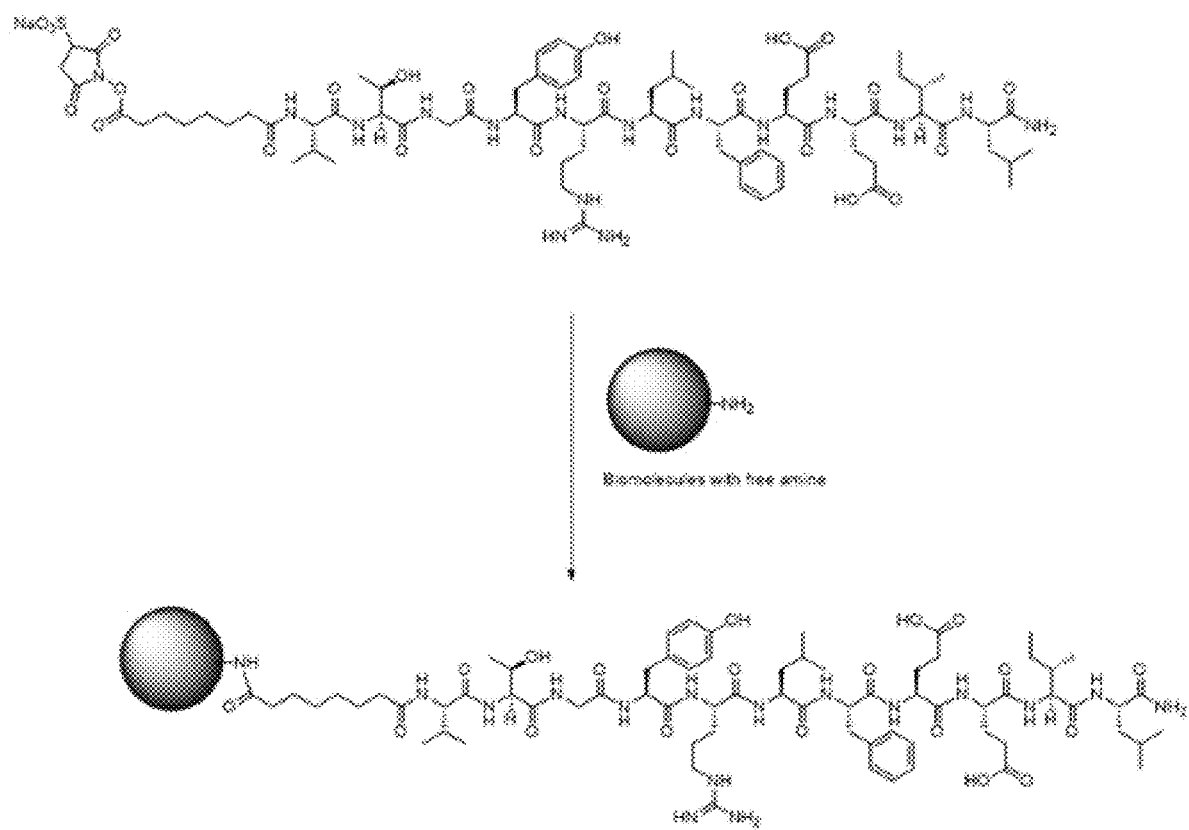
FIG. 2. Synthetic scheme for attaching a sulfo-SE peptide to a generic biomolecule.

In some embodiments, provided herein are methods for the labeling of biomolecules with reactive sulfo-SE peptides (FIG. 2). In some embodiments, a biomolecule is combined with sulfo-SE peptide (e.g., under appropriate reaction conditions (e.g., pH 4-9, pH 7-8.5 (e.g., NaHCO$_3$ solution (pH 8.5)) to produce a peptide-labeled biomolecule through the reaction of the sulfo-SE group with an amine (e.g., primary amine) on the biomolecule (e.g., on the surface of the biomolecule, a solvent accessible amine, etc.).

Some embodiments herein find use in attaching bioluminescent peptides or polypeptides, or components of bioluminescent complexes (e.g., peptide capable of forming a complex with one or more other peptide/polypeptide components) to biomolecules of interest. In some embodiments, such labeled biomolecules are used in bioluminescent-based assays and platforms. Some embodiments herein utilize a NanoLuc-based bioluminescent platform or NanoLuc-based bioluminescent complementation platform (See, e.g., WO/2014/151736 (Intl. App. No. PCT/US2014/026354) and U.S. Pro. App. No. 62/684,014; herein incorporated by reference in their entireties).

Figure 3A:
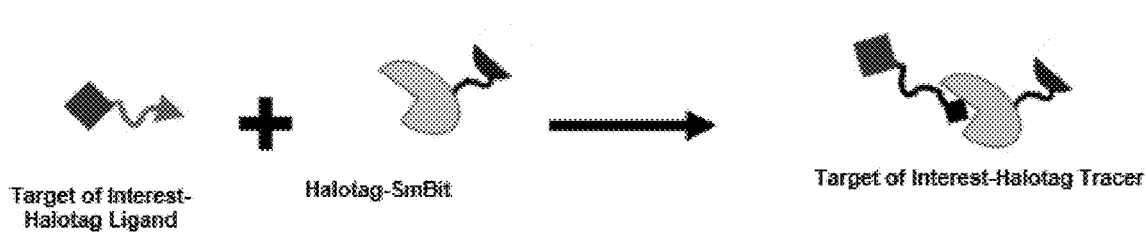
FIG. 3A-B. Attachment of the SmBiT peptide to a target of interest via (A) HaloTag and (B) biotin/streptavidin systems.
Figure 3B:
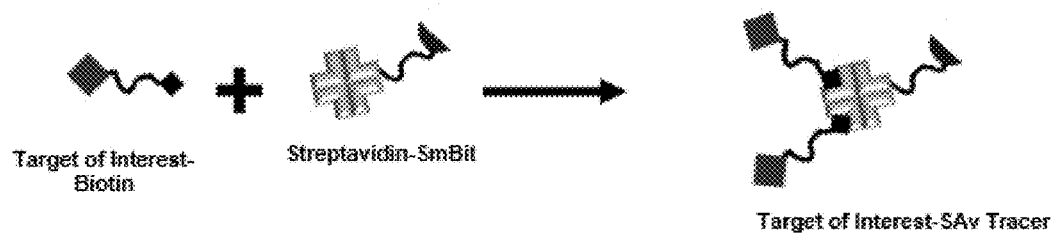

NanoLuc® Binary Technology (NanoBiT) is a structural complementation reporter designed for biomolecular interaction studies. The NanoBiT® system is composed of two small non-luminescent subunits, Large BiT (LgBiT; 18 kDa) and Small BiT (SmBiT; 11 amino acid peptide) that have been optimized for stability and minimal self-association. When two biomolecular components labeled with these subunits come in close proximity, the subunits come together to form an active enzyme and generate a bright luminescent signal. The small subunit size of the NanoBiT complementation partners minimizes interference with protein functionality, and the bright signal allows sensitive detection. HaloTag and biotin/streptavidin systems have been the most common methods to link the NanoBiT components to the targets of interests (FIG. 3). However, both methods impose the significant complexity for labeling a small peptide to the targets of interests and are also limited by the large size of HaloTag or streptavidin as the linkage to form the optimal complementary active enzyme and generate a bright luminescent signal.

Figure 4:
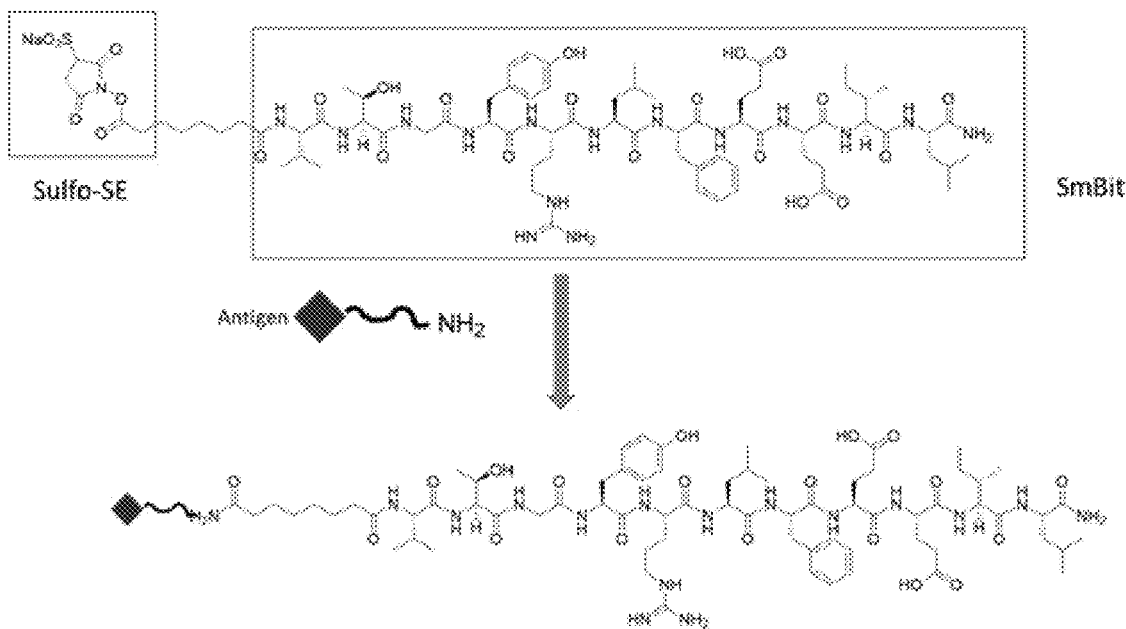
FIG. 4. SmBiT-Sulfo-SE labeling of an antigen.
Figure 5:
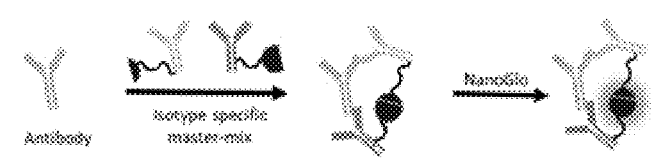
FIG. 5. Evaluation of SE-SmBiT-labeled Goat anti-mouse antibody in a direct immunoassay.
Figure 5:
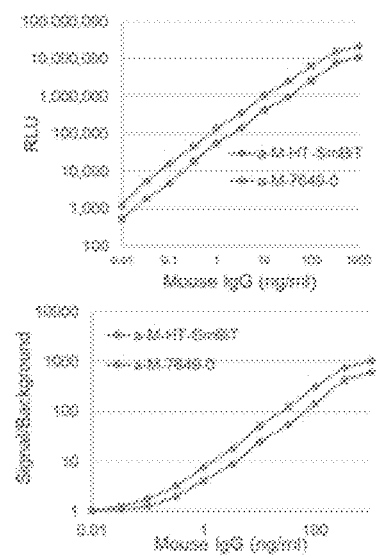
Figure 6:
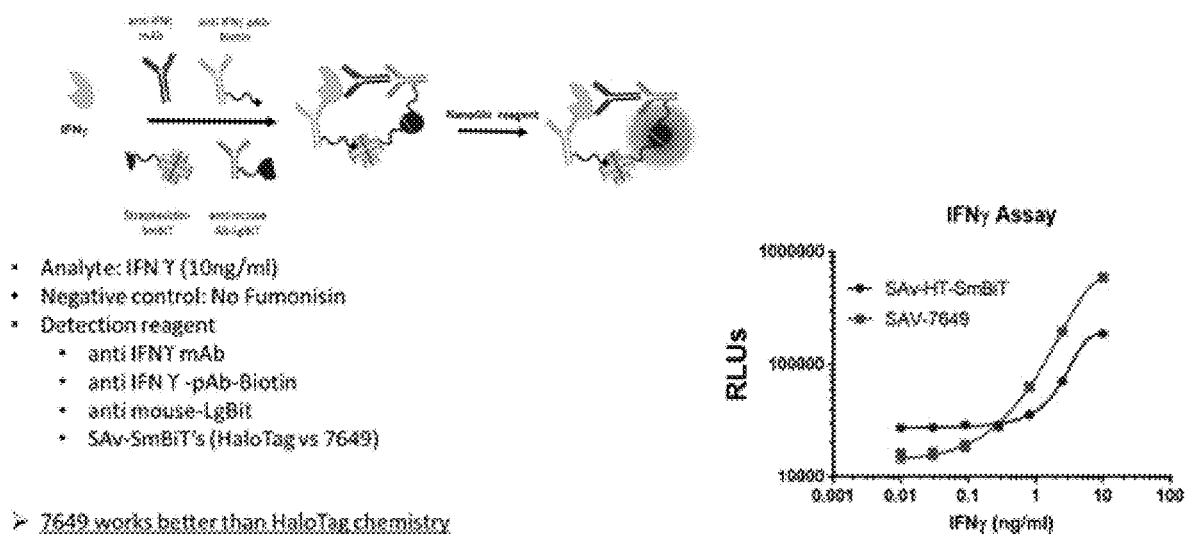
FIG. 6. Evaluation of SE-SmBiT-labeled Streptavidin in an IFNγ indirect immunoassay.
Figure 7:
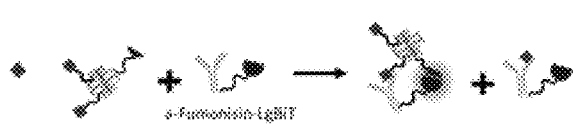
FIG. 7. Evaluation of SE-SmBiT-labeled Streptavidin in a fumonisin competition immunoassay.
Figure 7:
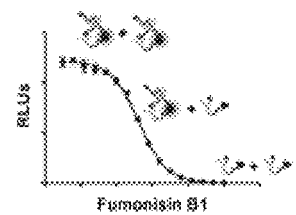
Figure 7:
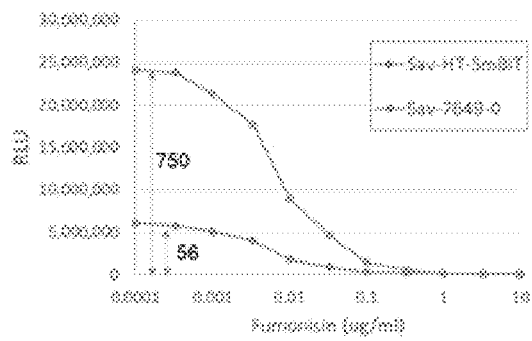
Figure 8:
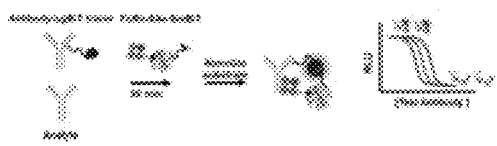
FIG. 8. Evaluation of SE-SmBiT-labeled Streptavidin in an FcRn binding assay.
Figure 8:
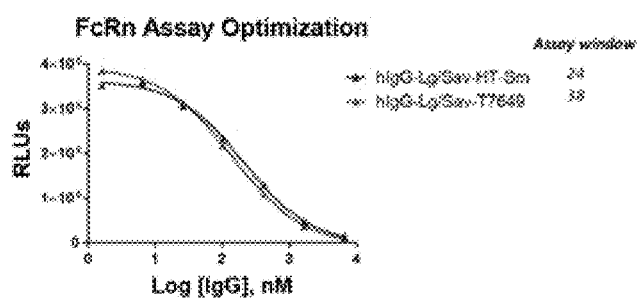
Figure 9:
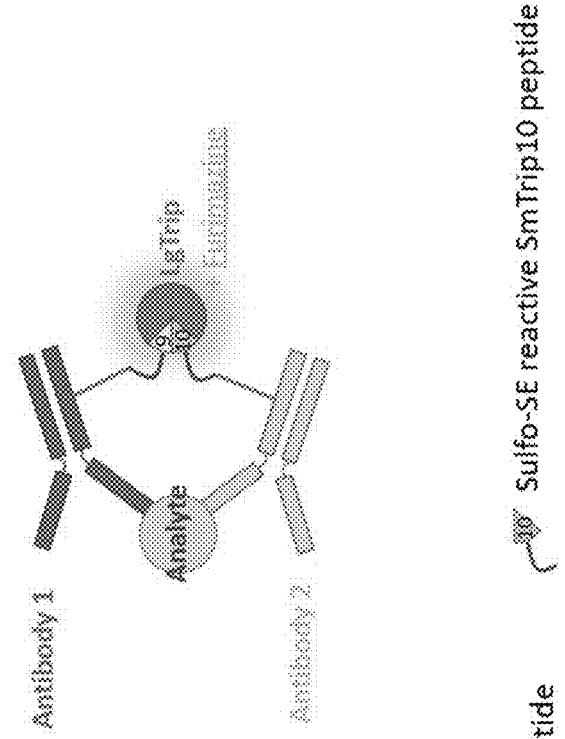
FIG. 9. Schematic illustration depicting exemplary bioluminescent immunoassay using components and reagents described herein.
Figure 9:
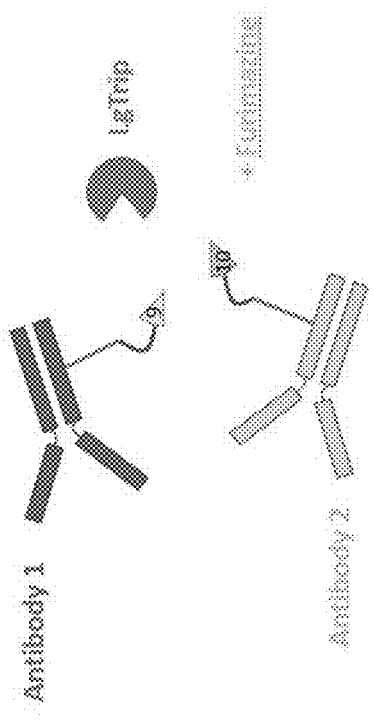

Experiments conducted during development of embodiments herein demonstrate synthesis of a stable (e.g., not autoreactive) sulfo-SE/peptide conjugate (e.g., using the SmBiT peptide). Experiments were also conducted to demonstrate peptide labeling of biomolecules (e.g., antibodies, streptavidin) with a peptide (sulfo-SE-SmBiT) at primary amines via a one-step SE protein labeling protocol (FIG. 4).

Embodiments herein find use in attaching a reactive sulfo-SE group to peptides or polypeptides with. The sulfo-SE group allows the peptides or polypeptides to be conjugated to suitable biomolecules that display an accessible amine group (e.g., primary amine). In some embodiments, any peptides lacking lysine and cysteine amino acids (lacking accessible lysine and cysteine amino acids) is suitable for sulfo-SE labeling via the methods described herein. In some embodiments, even peptides comprising one or more (e.g., 1, 2, 3, 4, 5, 6, 7, 8, 9, 10, or more) reactive nucleophilic amino acids (e.g., serine, threonine, arginine, tyrosine, glutamic acid, aspartic acid) are amenable to sulfo-SE-labeling by the methods herein.

In some embodiments, an SE-sulfo group on a peptide is utilized to attach the peptide to a biomolecule or other analyte for use in a bioluminescent complementation system. In some embodiments, peptide and polypeptide components are non-luminescent in the absence of complementation and/or complementation enhances bioluminescence of a peptide or polypeptide component. In some embodiments, target analyte binding agents (e.g., antibodies, antibody fragments, etc.) are labeled with sulfo-SE-tagged peptide components of the bioluminescent complexes described herein. For example, embodiments of the present disclosure utilize sulfo-SE labeling to incorporate NanoLuc-based technologies (e.g., NanoBit, NanoTrip, Nano-Glo, NanoBRET, etc.) into target analyte detection assays.

In some embodiments, provided herein are assays and platforms using sulfo-SE peptides to incorporate bioluminescent polypeptides and/or bioluminescent complexes (of peptide(s) and/or polypeptide components) based on (e.g., structurally, functionally, etc.) the luciferase of *Oplophorus gracilirostris*, the NanoLuc luciferase (Promega Corporation; U.S. Pat. Nos. 8,557,970; 8,669,103; herein incorporated by reference in their entireties), and/or the NanoBiT (U.S. Pat. No. 9,797,889; herein incorporated by reference in its entirety) or NanoTrip (U.S. Prov. App. No. 62/684,014; herein incorporated by reference in its entirety). As described below, in some embodiments, the assays, devices, and systems herein incorporate commercially available NanoLuc-based technologies (e.g., NanoLuc luciferase, NanoBRET, NanoBiT, NanoTrip, Nano-Glo, etc.), but in other embodiments, various combinations, variations, or derivations from the commercially available NanoLuc-based technologies are employed.

PCT Appln. No. PCT/US2010/033449, U.S. Pat. No. 8,557,970, PCT Appln. No. PCT/2011/059018, and U.S. Pat. No. 8,669,103 (each of which is herein incorporated by reference in their entirety and for all purposes) describe compositions and methods comprising bioluminescent polypeptides; such polypeptides find use in embodiments herein and can be used in conjunction with the assays and methods described herein PCT Appln. No. PCT/US14/26354 and U.S. Pat. No. 9,797,889 (each of which is herein incorporated by reference in their entirety and for all purposes) describe compositions and methods for the assembly of bioluminescent complexes (e.g., via the NanoBiT system); such complexes, and the peptide and polypeptide components thereof, find use in embodiments herein and can be used in conjunction with the assays and methods described herein. In some embodiments, sulfo-SE tagging of peptides is used to create reactive peptides for linking to biomolecules of interests. In some embodiments, any NanoBiT-based peptides or polypeptides are linked (e.g., fused, chemically linked, etc.) to a binding element or other component of the assays and systems described herein using the methods described herein.

In some embodiments, provided herein are peptides having at least 60% (e.g., 06%, 65%, 70%, 75%, 80%, 85%, 90%, 95%, 96%, 97%, 98%, 99%, 100%, or ranges therebetween) sequence identity with SEQ ID NO: 10 (SmBiT), but less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and SEQ ID NO: 8. In some embodiments, such a peptide is reacted with bis-sulfo-SE to produce a sulfo-SE peptide. In some embodiments, provided herein are sulfo-SE peptides (N-terminal labeled) comprising at least 60% (e.g., 06%, 65%, 70%, 75%, 80%, 85%, 90%, 95%, 96%, 97%, 98%, 99%, 100%, or ranges therebetween) sequence identity with SEQ ID NO: 10 (SmBiT), but less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and SEQ ID NO: 8, wherein the peptide does not comprise lysine or cysteine. In some embodiments, provided herein are sulfo-SE peptides comprising SEQ ID NO: 10 (SmBiT), wherein the peptide does not comprise lysine or cysteine. In some embodiments, provided herein are methods of conjugating such peptides to amines displayed on biomolecules. In some embodiments, provided herein are biomolecules displaying such peptides, following reaction of the sulfo-SE groups on the peptides with amines on the biomolecules. assays and systems described herein using the methods described herein.

In some embodiments, provided herein are polypeptides having at least 60% (e.g., 06%, 65%, 70%, 75%, 80%, 85%, 90%, 95%, 96%, 97%, 98%, 99%, 100%, or ranges therebetween) sequence identity with SEQ ID NO: 9 (LgBiT), but less than 100% (e.g., <99%, <98%, <97%, <96%, <95%, <94%, <93%, <92%, <91%, <90%) sequence identity with SEQ ID NO: 1, SEQ ID NO: 2, SEQ ID NO: 5, and SEQ ID NO: 6. In some embodiments, such polypeptides for bioluminescent complexes with complement peptides displayed on biomolecules (following reaction of the sulfo-SE groups on the peptides with amines on the biomolecules).

U.S. Prov. App. No. 62/684,014; herein incorporated by reference in its entirety and for all purposes) describes compositions and methods for the assembly of bioluminescent complexes (e.g., via the NanoTrip system); such complexes, and the peptides and polypeptide components thereof, find use in embodiments herein and can be used in conjunction with the assays and methods described herein. In some embodiments, sulfo-SE attachment to peptides is used to create reactive peptides for linking to biomolecules of interests. In some embodiments, any of the aforementioned NanoTrip-based peptides or polypeptides are linked (e.g., fused, chemically linked, etc.) to a binding element or other component of the assays and systems described herein.

In some embodiments, provided herein are peptides having at least 60% (e.g., 06%, 65%, 70%, 75%, 80%, 85%, 90%, 95%, 96%, 97%, 98%, 99%, 100%, or ranges therebetween) sequence identity with SEQ ID NO: 11 (HiBiT), but less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and SEQ ID NO: 8. In some embodiments, such a peptide is reacted with bis-sulfo-SE to produce a sulfo-SE peptide. In some embodiments, provided herein are sulfo-SE peptides (N-terminal labeled) comprising at least 60% (e.g., 06%, 65%, 70%, 75%, 80%, 85%, 90%, 95%, 96%, 97%, 98%, 99%, 100%, or ranges therebetween) sequence identity with SEQ ID NO: 11 (HiBiT), but less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and SEQ ID NO: 8, wherein the peptide does not comprise lysine or cysteine. In some embodiments, provided herein are sulfo-SE peptides comprising a lysine- and cysteine-free variant of SEQ ID NO: 11 (HiBiT), wherein the peptide does not comprise lysine or cysteine (e.g., any C or K residues are conservatively substituted). In some embodiments, provided herein are methods of conjugating such peptides to amines displayed on biomolecules. In some embodiments, provided herein are biomolecules displaying such peptides, following reaction of the sulfo-SE groups on the peptides with amines on the biomolecules.

In some embodiments, provided herein are peptides having at least 60% (e.g., 06%, 65%, 70%, 75%, 80%, 85%, 90%, 95%, 96%, 97%, 98%, 99%, 100%, or ranges therebetween) sequence identity with SEQ ID NO: 13 (SmTrip9), but less than 100% (e.g., <99%, <98%, <97%, <96%, <95%, <94%, <93%, <92%, <91%, <90%) sequence identity with SEQ ID NO: 1, SEQ ID NO: 3, SEQ ID NO: 5, and SEQ ID NO: 7. In some embodiments, such a peptide is reacted with bis-sulfo-SE to produce a sulfo-SE peptide. In some embodiments, provided herein are sulfo-SE peptides (N-terminal labeled) comprising at least 60% (e.g., 06%, 65%, 70%, 75%, 80%, 85%, 90%, 95%, 96%, 97%, 98%, 99%, 100%, or ranges therebetween) sequence identity with SEQ ID NO: 13 (SmTrip9), but less than 100% (e.g., <99%, <98%, <97%, <96%, <95%, <94%, <93%, <92%, <91%, <90%) sequence identity with SEQ ID NO: 1, SEQ ID NO: 3, SEQ ID NO: 5, and SEQ ID NO: 7, wherein the peptide does not comprise lysine or cysteine. In some embodiments, provided herein are sulfo-SE peptides comprising SEQ ID NO: 13 (SmTrip9), wherein the peptide does not comprise lysine or cysteine (e.g., any C or K residues are conservatively substituted). In some embodiments, provided herein are methods of conjugating such peptides to amines displayed on biomolecules. In some embodiments, provided herein are biomolecules displaying such peptides, following reaction of the sulfo-SE groups on the peptides with amines on the biomolecules.

In some embodiments, provided herein are peptides having at least 60% (e.g., 06%, 65%, 70%, 75%, 80%, 85%, 90%, 95%, 96%, 97%, 98%, 99%, 100%, or ranges therebetween) sequence identity with SEQ ID NO: 14 (β9/β10 dipeptide), but less than 100% (e.g., <99%, <98%, <97%, <96%, <95%, <94%, <93%, <92%, <91%, <90%) sequence identity with SEQ ID NO: 1, SEQ ID NO: 3, SEQ ID NO: 4, SEQ ID NO: 5, SEQ ID NO: 7, and SEQ ID NO: 8. In some embodiments, such a peptide is reacted with sulfo-NHS to produce a sulfo-SE peptide. In some embodiments, provided herein are sulfo-SE peptides (N-terminal labeled) comprising at least 60% (e.g., 06%, 65%, 70%, 75%, 80%, 85%, 90%, 95%, 96%, 97%, 98%, 99%, 100%, or ranges therebetween) sequence identity with SEQ ID NO: 14 (β9/β10 dipeptide), but less than 100% (e.g., <99%, <98%, <97%, <96%, <95%, <94%, <93%, <92%, <91%, <90%) sequence identity with SEQ ID NO: 1, SEQ ID NO: 3, SEQ ID NO: 4, SEQ ID NO: 5, SEQ ID NO: 7, and SEQ ID NO: 8, wherein the peptide does not comprise lysine or cysteine. In some embodiments, provided herein are sulfo-SE peptides comprising SEQ ID NO: 14 (β9/β10 dipeptide), wherein the peptide does not comprise lysine or cysteine (e.g., any C or K residues are conservatively substituted). In some embodiments, provided herein are methods of conjugating such peptides to amines displayed on biomolecules. In some embodiments, provided herein are biomolecules displaying such peptides, following reaction of the sulfo-SE groups on the peptides with amines on the biomolecules.

In some embodiments, provided herein are polypeptides having at least 60% (e.g., 06%, 65%, 70%, 75%, 80%, 85%, 90%, 95%, 96%, 97%, 98%, 99%, 100%, or ranges therebetween) sequence identity with a lysine- and cysteine-free variant of SEQ ID NO: 12 (LgTrip), but less than 100% (e.g., <99%, <98%, <97%, <96%, <95%, <94%, <93%, <92%, <91%, <90%) sequence identity with SEQ ID NO: 1, SEQ ID NO: 2, SEQ ID NO: 5, SEQ ID NO: 6, and SEQ ID NO: 9. In some embodiments, such polypeptides for bioluminescent complexes with complement peptides displayed on biomolecules (following reaction of the sulfo-SE groups on the peptides with amines on the biomolecules).

In some embodiments, provided herein are peptides having at least 60% (e.g., 06%, 65%, 70%, 75%, 80%, 85%, 90%, 95%, 96%, 97%, 98%, 99%, 100%, or ranges therebetween) sequence identity with one or more of SEQ ID NOS: 15, 16, 17, 18, 19, 20, 21, 22, 23, 24, 25, 26, 27, 28, 29, 30, 31, 32, 33, 34, 35 or 36. In some embodiments, a peptide comprises less than 100% (e.g., <99%, <98%, <97%, <96%, <95%, <94%, <93%, <92%, <91%, <90%) sequence identity with any naturally occurring (e.g., SEQ ID NOS: 1-4) or commercial (e.g., SEQ ID NOS: 5-8)

sequences provided herein. In some embodiments, such a peptide is reacted with bis-sulfo-SE to produce a sulfo-SE peptide. In some embodiments, provided herein are sulfo-SE peptides (N-terminal labeled) comprising at least 60% (e.g., 06%, 65%, 70%, 75%, 80%, 85%, 90%, 95%, 96%, 97%, 98%, 99%, 100%, or ranges therebetween) sequence identity with one or more of SEQ ID NOS: 15, 16, 17, 18, 19, 20, 21, 22, 23, 24, 25, 26, 27, 28, 29, 30, 31, 32, 33, 34, 35 or 36, but less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and SEQ ID NO: 8, wherein the peptide does not comprise lysine or cysteine. In some embodiments, provided herein are sulfo-SE peptides comprising SEQ ID NOS: 15, 16, 17, 18, 19, 20, 21, 22, 23, 24, 25, 26, 27, 28, 29, 30, 31, 32, 33, 34, 35 or 36, wherein the peptide does not comprise lysine or cysteine. In some embodiments, provided herein are methods of conjugating such peptides to amines displayed on biomolecules. In some embodiments, provided herein are biomolecules displaying such peptides, following reaction of the sulfo-SE groups on the peptides with amines on the biomolecules.

As disclosed in PCT Appln. No. PCT/US13/74765 and U.S. patent application Ser. No. 15/263,416 (herein incorporated by reference in their entireties and for all purposes) describe bioluminescence resonance energy transfer (BRET) system and methods (e.g., incorporating NanoLuc-based technologies); such systems and methods, and the bioluminescent polypeptide and fluorophore-conjugated components thereof, find use in embodiments herein and can be used in conjunction with the assays and methods described herein In some embodiments, any of the NanoLuc-based, NanoBiT-based, and/or NanoTrip-based peptides (e.g., sulfo-SE peptides, biomolecule conjugated peptides, etc.), polypeptide, complexes, fusions, and conjugates may find use in BRET-based applications with the assays, methods, devices, and systems described herein. For example, an SmBiT peptide (or other NanoBiT- or NanoTrip-based peptide described herein) is linked to a biomolecule via the sulfo-SE technology described herein; a bioluminescent complex is formed when the peptide is brought into contact or proximity with one or more other components of the system (e.g., linked to some target of interest, linked to a binding agent, etc.); BRET is detected when the bioluminescent complex is brought into proximity or contact with a fluorescent molecule (e.g., linked to some target of interest, linked to a binding agent, etc.). In some embodiments, the emission spectrum of the NanoLuc-based, NanoBiT-based, and/or NanoTrip-based polypeptide, peptide, or complex overlaps the excitation spectrum of the fluorescent molecule (e.g., fluorophore). In some embodiments, the fluorescent molecule (e.g., fluorophore) is an energy acceptor. As used herein, the term "energy acceptor" refers to any small molecule (e.g., chromophore), macromolecule (e.g., autofluorescent protein, phycobiliproteins, nanoparticle, surface, etc.), or molecular complex that produces a readily detectable signal in response to energy absorption (e.g., resonance energy transfer). In certain embodiments, an energy acceptor is a fluorophore or other detectable chromophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLuoR (Invitrogen), DYLIGHT FLUOR (Thermo Scientific, Pierce), ATTO and TRACY (Sigma Aldrich), FluoProbes (Interchim), DY and MEGA-STOKES (Dyomics), SULFO CY dyes (CYANDYE, LLC), SETAU AND SQUARE DYES (SETA BioMedicals), QUASAR, and CAL FLUOR dyes (Biosearch Technologies), SURELIGHT DYES (APC, RPE, PerCP, Phycobilisomes) (Columbia Biosciences), APC, APCXL, RPE, BPE (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog), such as those described in U.S. patent application Ser. No. 13/682,589, herein incorporated by reference in its entirety.

As described above, the labeling technologies described herein are not limited to use with bioluminescent peptides, polypeptides, and complexes. Rather, the compositions, methods and systems herein find use as a general system for the attachment of peptides (e.g., peptide lacking a lysine and cysteine residue) to biomolecules or materials. The peptide-conjugated biomolecules generated herein find use in a variety of systems, reactions, reagents, platforms, and assays.

A particular application for the technologies described herein is linking peptides to biomolecules (e.g., antibodies, antibody fragments, antigens, etc.) for use in ligand binding and/or immunoassays. In some embodiments, the compositions and methods herein find use in attaching peptide components of immunoassays (e.g., antigens, components of bioluminescent complexes, etc.) to other immunoassay components (e.g., antibodies, antibody fragments, antigens, etc.). Embodiments herein find use in preparing reagents for, and/or are involved in the steps of, various immunoassays, such as competitive immunoassays, direct immunoassays, indirect immunoassays, enzyme linked immunosorbent assays (ELISA), sandwich immunoassay, combination immunoassays (e.g., See U.S. application Ser. No. 15/589, 557; herein incorporated by reference in its entirety), etc. In various embodiments, a sulfo-SE peptide tag (e.g., β9-like (e.g., SmTrip9) and β10-like (e.g., SmTrip10) peptides; β9/β10-like dipeptides; etc.) is tethered/fused to a primary or secondary antibody (e.g., at a primary amine) to provide a method of detection for a particular analyte. As another example, a sulfo-SE peptide tag is tethered/fused to an antibody-binding protein (e.g., protein A or protein G) and used to detect a specific antibody bound to a particular analyte (e.g., wherein the analyte is bound to the complementary peptide tag). As another example, a sulfo-SE peptide tag is tethered/fused to streptavidin and used to detect a specific biotinylated antibody bound to a particular analyte (e.g., wherein the analyte is bound to the complementary peptide tag). As yet another example, sulfo-SE peptide tags are tethered/fused to primary and secondary antibodies, where the primary antibody recognizes a particular analyte, and the secondary antibody recognizes the primary antibody. As still another example, a sulfo-SE peptide tag is tethered/fused to an analyte and used in a competitive sandwich ELISA format. A sulfo-SE peptide tag is tethered/fused conjugated to an analyte may also be used to detect antibodies capable of binding the analyte.

Various embodiments herein find use in small molecule or other biomolecule detection via immunoassay. Exemplary embodiments comprise the use of a small molecule or other biomolecule directly (e.g., identical or similar to the target small molecule) labeled with a first sulfo-SE peptide tag (e.g., a first peptide component of a bioluminescent complex) described herein and a binding moiety for the target small molecule or biomolecule is fused or linked to a second sulfo-SE peptide tag (e.g., a second peptide component of a bioluminescent complex) described herein. In the presence of detection reagents (e.g., polypeptide component of the bioluminescent complex and substrate (e.g., coelenterazine or coelenterazine analog)), a bioluminescent signal is produced by the system. When the system is exposed to a sample (e.g., biological sample, environmental sample, etc.), the bioluminescent signal will be reduced if the small molecule or biomolecule target is present in the sample (the labeled small molecule or biomolecule will be competed out of the complex allowing, in some cases, quantitation of the small molecule or biomolecule target). Alternative configurations for such assays are also within the scope herein (e.g., a biomolecular complex comprising a single sulfo-SE component).

In some embodiments, the analyte for an immunoassay is a toxin (e.g., mycotoxin, etc.), metabolite (e.g., amino acid, glucose molecule, fatty acid, nucleotide, cholesterol, steroid, etc.), vitamin (e.g., vitamin A, vitamin B1, vitamin B2, Vitamin B3, vitamin B5, vitamin B7, vitamin B9, vitamin B12, vitamin C, vitamin D, vitamin E, vitamin H or vitamin K, etc.), coenzyme or cofactor (e.g., coenzyme A, coenzyme B, coenzyme M, coenzyme Q, cytidine triphosphate, acetyl coenzyme A, reduced nicotinamide adenine dinucleodtide (NADH), nicotinamide adenine (NAD+), nucleotide adenosine monophosphoate, nucleotide adenosine triphosphate, glutathione, heme, lipoamide, molybdopterin, 3'-phosphoadenosine-5'-phsphosulfate, pyrroloquinoline quinone, tetrahydrobiopterin, etc.), biomarker or antigen (e.g., erythropoietin (EPO), ferritin, folic acid, hemoglobin, alkaline phosphatase, transferrin, apolipoprotein E, CK, CKMB, parathyroid hormone, insulin, cholesteryl ester transfer protein (CETP), cytokines, cytochrome c, apolipoprotein AI, apolipoprotein AII, apolipoprotein BI, apolipoprotein B-100, apolipoprotein B48, apolipoprotein CII, apolipoprotein CIII, apolipoprotein E, triglycerides, HD cholesterol, LDL cholesterol, lecithin cholesterol acyltransferase, paraxonase, alanine aminotransferase (ALT), asparate transferase (AST), CEA, HER-2, bladder tumor antigen, thyroglobulin, alpha-fetoprotein, PSA, CA 125, CA 19.9, CA 15.3, leptin, prolactin, osteoponitin, CD 98, fascin, troponin I, CD20, HER2, CD33, EGFR, VEGFA, etc.), drug (cannabinoid (e.g., tetrahydrocannabinol (THC), cannabidiol (CBD) and cannabinol (CBN), etc.), opioid (e.g., heroin, opium, fentanyl, etc.), stimulant (e.g., cocaine, amphetamine, methamphetamine, etc.), club drug (e.g., MDMA, flunitrazepam, gama-hydroxybutyrate, etc.), dissociative drug (e.g., ketamine, phencyclidine, salvia, dextromethorphan, etc.), hallucinogens (e.g., LSD, mescaline, psilocybin, etc.), etc.), explosive (e.g., 2,4,6-trinitrotoluene (TNT) and hexahydro-1,3,5-trinitro-1,3,5-triazine (RDX), pentaerythritol tetranitrate (PETN), etc.), toxic chemical (e.g., tabun (GA), sarin (GB), soman (GD), cyclosarin (GF), 2-(dimethylamino)ethyl N, N-dimethylphosphoramidofluoridate (GV), VE, VG, VM, VP, VR, VS, or VX nerve agent), etc.

In some embodiments, the sulfo-SE peptide is attached to the analyte. In some embodiments, the sulfo-SE peptide is attached to an antibody or antibody fragment for the analyte. In some embodiments, the sulfo-SE peptide is attached to streptavidin. In some embodiments, the sulfo-SE peptide is attached to HaloTag. In some embodiments, sulfo-SE peptide is attached to a solid surface. Various immunoassays or other assays can be carried out using such reagents and are within the scope herein.

The sulfo-SE peptides, and biomolecules labeled with the sulfo-SE peptides herein (and methods of preparation thereof), find use in a wide variety of applications and formats. The following are non-exhaustive exemplary examples of methods and formats utilizing the systems described herein:

Intracellular, two protein systems for dynamic protein-protein interaction analysis with peptide-labeled proteins expressed as fusions via traditional transfection or endogenously tagged proteins via CRISPR;

Intracellular, three protein systems for dynamic protein-protein interaction analysis with peptide-labeled proteins expressed as fusions via traditional transfection or as endogenously-tagged proteins generated via CRISPR;

Target specific assays for analyte measurement by gain of signal (e.g. diagnostic test, non-cellular, etc.);

Target specific competition assays for analyte measurement through loss of signal (e.g. diagnostic test, non-cellular, etc.);

Homogeneous assays using peptide tag-labelled recognition elements for detection/quantification of a single analyte or multiple analytes;

Detection of analyte(s) in liquid/solution phase or solid phase.

Surface-based assays (e.g., plate-based (e.g., microtiter plate), paper-based (e.g., Whatman protein saver 903 cards), plastic-based, swab-based, cuvette-based, membrane-based (e.g., PVDF, nitrocellulose, etc.), etc.;

Lateral flow and other capillary driven based methods;

Plate-based for solution phase assay (e.g., performed in a multiplexed dot blot/spot array assay format);

Aerosol-based detection;

Isothermal amplification of nucleic acids;

Rapid cycling PCR detection of nucleic acids;

Detection of protein-protein interaction;

Detection of native proteins in heterogeneous solutions;

Peptide-tagged complimentary recognition elements hybridize to a nucleic acid target sequence in tandem;

FISH-like applications utilizing bioluminescence or BRET for detection/quantification;

Detection of nucleic acids (e.g., single stranded and/or double stranded DNA and/or RNA);

Lab-on-chip and/or microfluidics applications;

Heterogeneous assays such as immunoassays (e.g., PCR amplification combined with homogeneous immunoassay analysis);

Etc.

Embodiments herein are not limited by the end uses of the sulfo-SE peptides and biomolecules labeled therewith.

Although embodiments herein are described as useful for linking a peptide (e.g., labeled with a sulfo-SE group) to various biomolecules, embodiments herein are not so limited. In some embodiments, sulfo-SE peptides are reacted with other molecules, molecular entities, materials, etc. in order to link and/or immobilize the peptide thereto. For example, a sulfo-SE peptide may be attached to a solid surface (e.g., beads (e.g., magnetic beads), chips, tubes, plates, particles, membranes, paper, etc.) that displays an amine group using the chemistry and reagents described herein.

EXPERIMENTAL

Experiments were conducted during development of embodiments herein to demonstrate the synthesis of sulfo-SE SmBiT peptides, conjugation of sulfoSE and peptide with different linkers, and conjugation of sulfo-SE-SmBiT with other moieties such as fluorophores, to demonstrate the utility of peptide-Sulfo-SE labeling of various antigens and the usefulness of such labeled antigens in various assay formats with various target antigens, the utility of peptide direct labeling, etc. These experiments demonstrate a portion of the breadth of the useful applications of the present technology but should not be viewed as limiting of the scope herein.

Example 1

SulfoSE-SmBiT Peptide (7649)

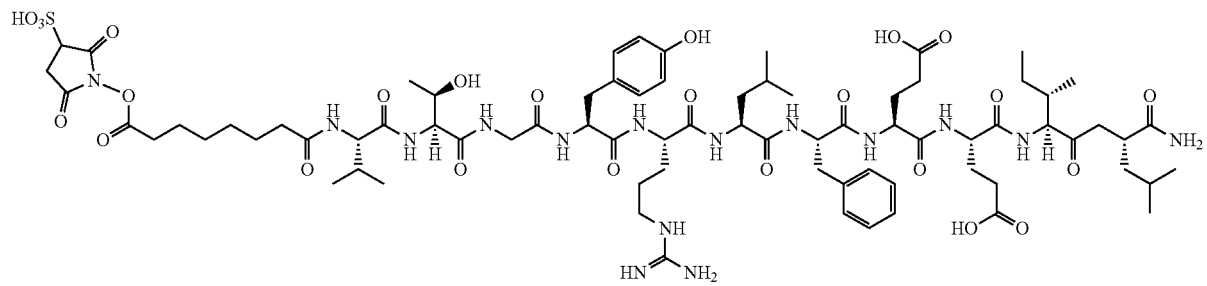 [SMILES: CC[C@H](C)[C@H](NC(=O)[C@H](CCC(=O)O)NC(=O)[C@H](CCC(=O)O)NC(=O)[C@H](Cc1ccccc1)NC(=O)[C@H](CC(C)C)NC(=O)[C@H](CCCNC(=N)N)NC(=O)[C@H](Cc1ccc(O)cc1)NC(=O)CNC(=O)[C@@H](NC(=O)[C@@H](NC(=O)CCCCCCC(=O)ON1C(=O)CC(S(=O)(=O)O)C1=O)C(C)C)[C@@H](C)O)C(=O)C[C@@H](CC(C)C)C(N)=O]

Small Bit peptide (VTGYRLFEEIL, 6 mg, 0.0045 mmol) was dissolved in a minimum amount of DMF and then added to a solution of BS3 (bis(sulfosuccinimidyl)suberate) (13 mg, 0.013 mmol) in phosphate buffer (0.5 M, pH=7.4). The reaction mixture was stirred for 1 h and directly purified by preparative HPLC. Calculated: m/z=1672.79 [M+H]$^+$; measured (ESI): m/z=1672.75.

Example 2

SulfoSE-SmTrip9 (691) (7962)

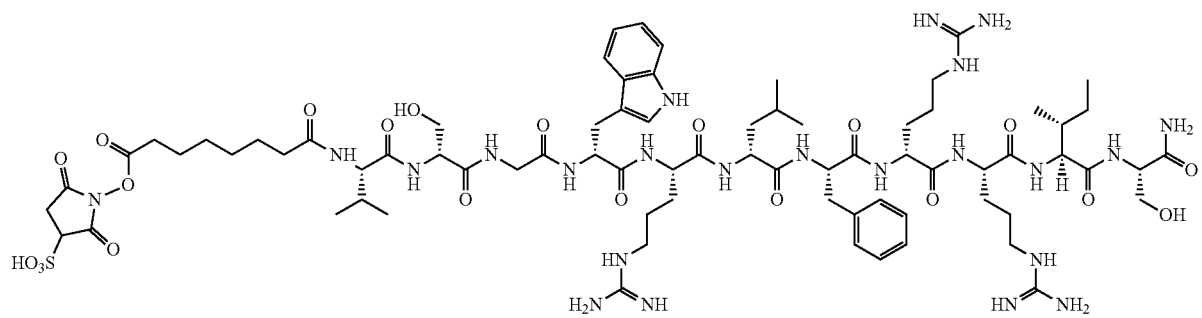 [SMILES: CC[C@@H](C)[C@H](NC(=O)[C@H](CCCNC(=N)N)NC(=O)[C@@H](CCCNC(=N)N)NC(=O)[C@H](Cc1ccccc1)NC(=O)[C@@H](CC(C)C)NC(=O)[C@H](CCCNC(=N)N)NC(=O)[C@@H](Cc1c[nH]c2ccccc12)NC(=O)CNC(=O)[C@@H](CO)NC(=O)[C@@H](NC(=O)CCCCCCC(=O)ON1C(=O)CC(S(=O)(=O)O)C1=O)C(C)C)C(=O)N[C@@H](CO)C(N)=O]

7962 was synthesized by the same method as 7649. Calculated: m/z=1707.85 [M+H]$^+$; measured (ESI): m/z=1707.75.

Example 3

SulfoSE-SmTrip9 (824) (8084)

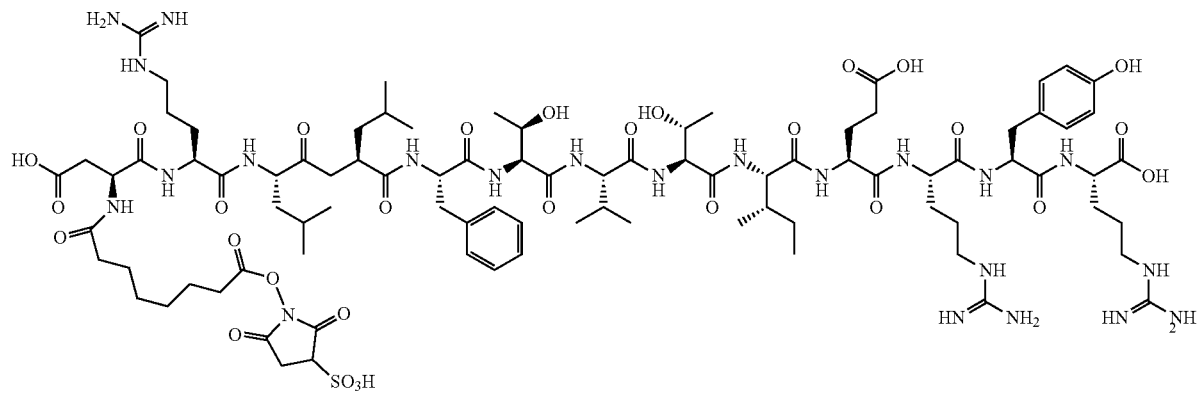 [SMILES: CC[C@H](C)[C@H](NC(=O)[C@@H](NC(=O)[C@@H](NC(=O)[C@@H](NC(=O)[C@H](Cc1ccccc1)NC(=O)[C@@H](CC(=O)[C@H](CC(C)C)NC(=O)[C@H](CCCNC(=N)N)NC(=O)[C@H](CC(=O)O)NC(=O)CCCCCCC(=O)ON1C(=O)CC(S(=O)(=O)O)C1=O)CC(C)C)[C@@H](C)O)C(C)C)[C@@H](C)O)C(=O)N[C@@H](CCC(=O)O)C(=O)N[C@@H](CCCNC(=N)N)C(=O)N[C@@H](Cc1ccc(O)cc1)C(=O)N[C@@H](CCCNC(=N)N)C(=O)O]

8084 was synthesized by the same method as 7649. Calculated: m/z=1006.99 [M+2H]$^{2+}$; measured (ESI): m/z=1006.32 [M+2H]$^{2+}$.

Example 4

SulfoSE-PEG3-SmTrip9 (693) (8134)

PEG3 bis Sulfo-SE

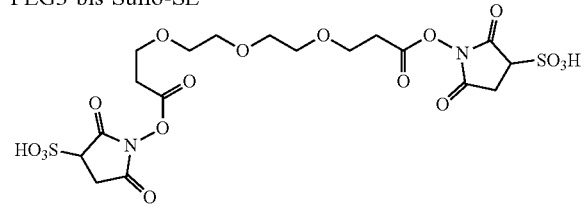

3,3'-((oxybis(ethane-2,1-diyl))bis(oxy))dipropionic acid (55 mg, 0.22 mmol) was dissolved in anhydrous DMF, and then diisopropylethylamine (120 mg, 0.88 mmol) and HATU (176 mg, 0.45 mmol) added. The mixture was stirred for five minutes. Meanwhile, N-hydroxy-2,5-dioxopyrrolidine-3-sulfonic acid (90 mg, 0.46 mmol) was dissolve in 5 ml DMSO, and then added to the previous solution dropwise. The mixture was stirred for another hour until LC-MS shows disappearance of acid. The solution was directly used in the next step. Calculated: m/z=603.05 [M$^-$]; measured (ESI): m/z=603.04 [M$^-$].

SulfoSE-PEG3-SmTrip9 (693) (8134)

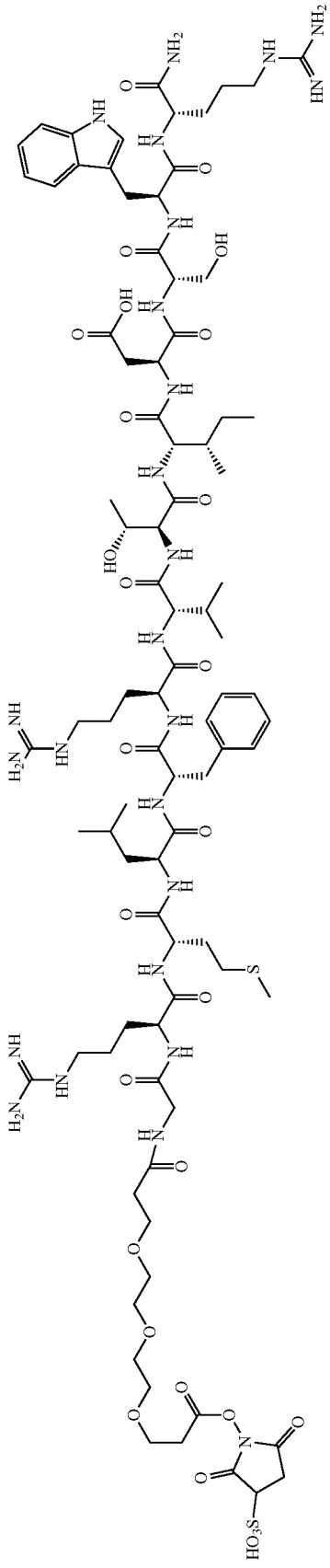

SmTrip9 (693) Peptide Trip521 (GRMLFRVTINSWR, 27 mg, 0.045 mmol) was dissolved in DMF. The solution was then added to the previous PEG3 bis Sulfo-SE solution. The mixture was then stirred for another hour and directly purified by preparative HPLC. Calculated: m/z=1022.98 $[M+2H]^{2+}$; measured (ESI): m/z=1023.09 $[M+2H]^{2+}$.

Example 5

SulfoSE-PEG3-SmTrip9 (691) (8118)

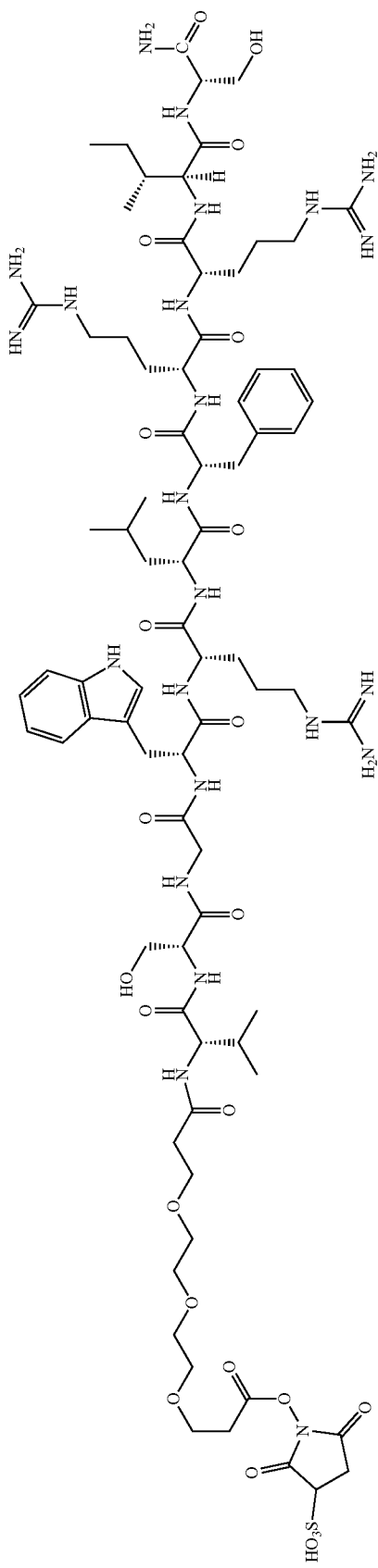

8084 was synthesized by the same method as 8134. Calculated: m/z=892.93 [M+2H]$^{2+}$; measured (ESI): m/z=893.61 [M+2H]$^{2+}$.

Example 6

SulfoSE-PEG3-SmTrip9 (895)-TAMRA (8160)

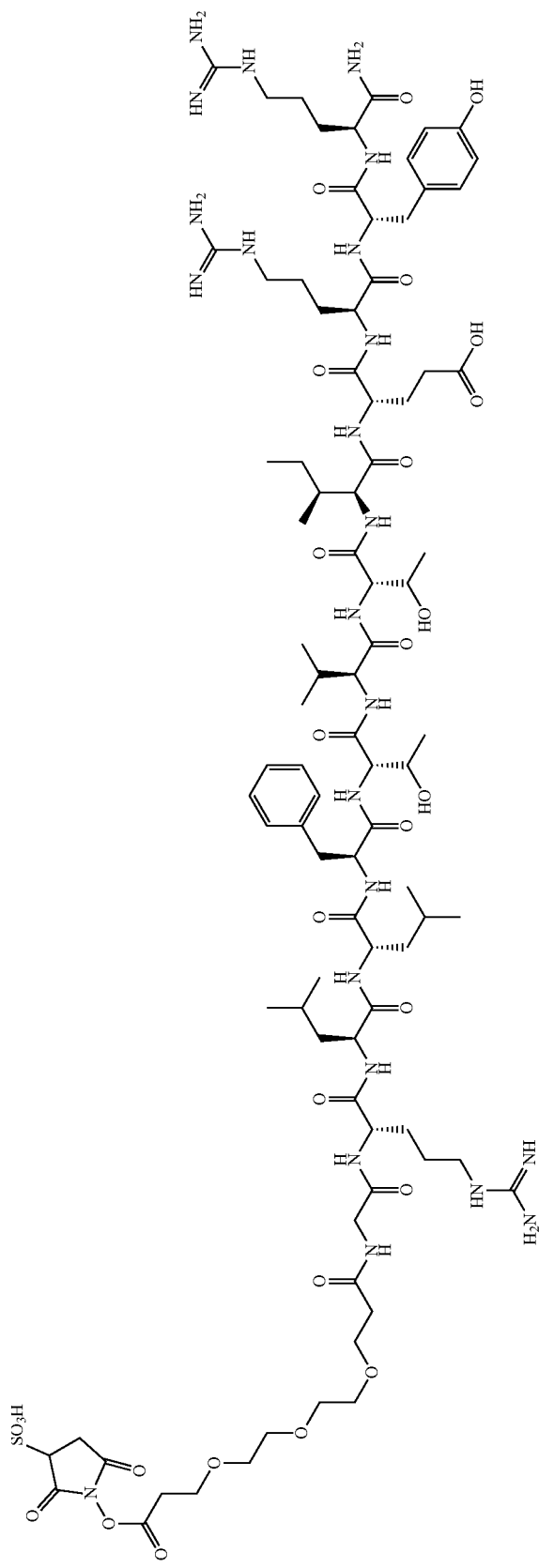

8160 was synthesized by the same method as 8134. Calculated: m/z=1016.51 [M+2H]$^{2+}$; measured (ESI): m/z=1016.92 [M+2H]$^{2+}$.

Example 7

SulfoSE-PEG3-SmTrip9 (938)-TAMRA (8136)

TAMRA-Maleimide

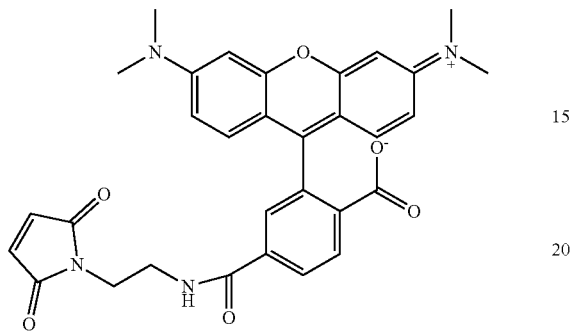

5-TAMRA (50 mg, 0.116 mmol) was dissolved in DMF. Diisopropylethylamine (45 mg, 0.128 mmol) was added followed by TSTU (38 mg, 0.128 mmol). The mixture was stirred for 20 min, and 1-(2-aminoethyl)-1H-pyrrole-2,5-dione (18 mg, 0.128 mmol) was added. The resulting reaction mixture was stirred for another hour and directly purified by preparative HPLC.

Calculated: m/z=553.20 [M+H]$^+$; measured (ESI): m/z=553.40.

SmTrip9 (938)-TAMRA

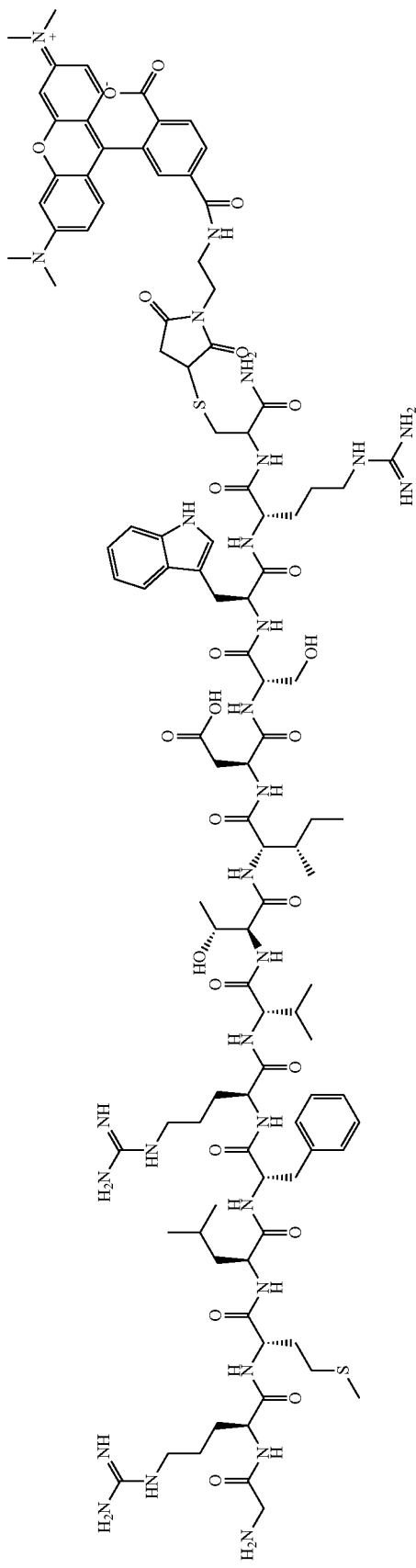

TAMRA-Maleimide (8 mg, 0.014 mmol) was dissolved in DMF. A solution of SmTrip9 (938) (GRMLFRVTINSWRC, 25 mg, 0.014 mmol) in PBS buffer (pH 7.4, 200 mM) was added. The reaction mixture was stirred for two hours and directly purified by preparative HPLC. Calculated: m/z=1146.05 $[M+2H]^{2+}$; measured (ESI): m/z=1146.33 $[M+2H]^{2+}$.

SulfoSE-PEG3-SmTrip9 (938)-TAMRA (8136)

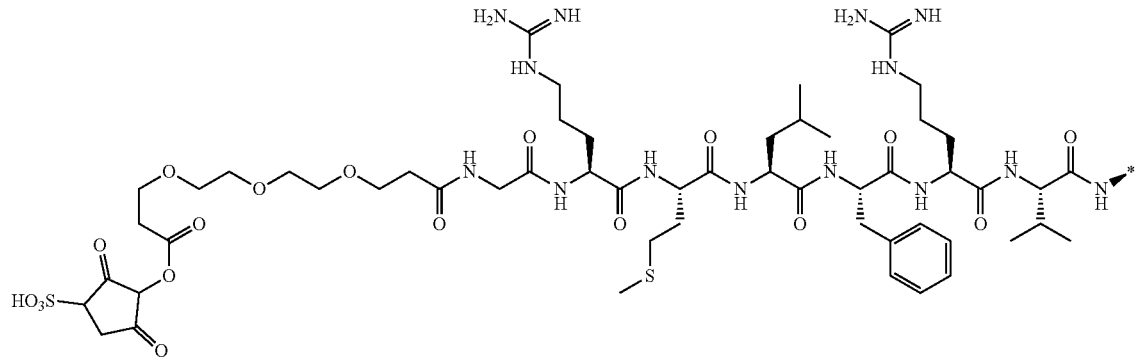

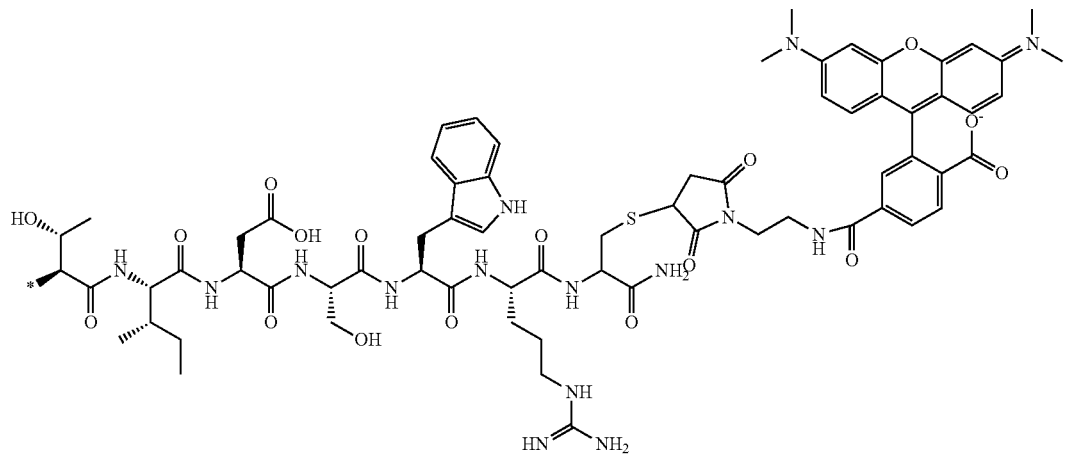

SmTrip9 (938)-TAMRA (8.5 mg, 0.0038 mmol) was dissolved in DMF. The solution was then added to PEG3 bis Sulfo-SE prepared as shown in Example 2. The reaction mixture was stirred for two hours and directly purified by preparative HPLC. Calculated: m/z=901.05 $[M+3H]^{3+}$; measured (ESI): m/z=901.20 $[M+3H]^{3+}$.

Example 8

SulfoSE-PEG3-SmTrip9 (937)-TAMRA (8135)

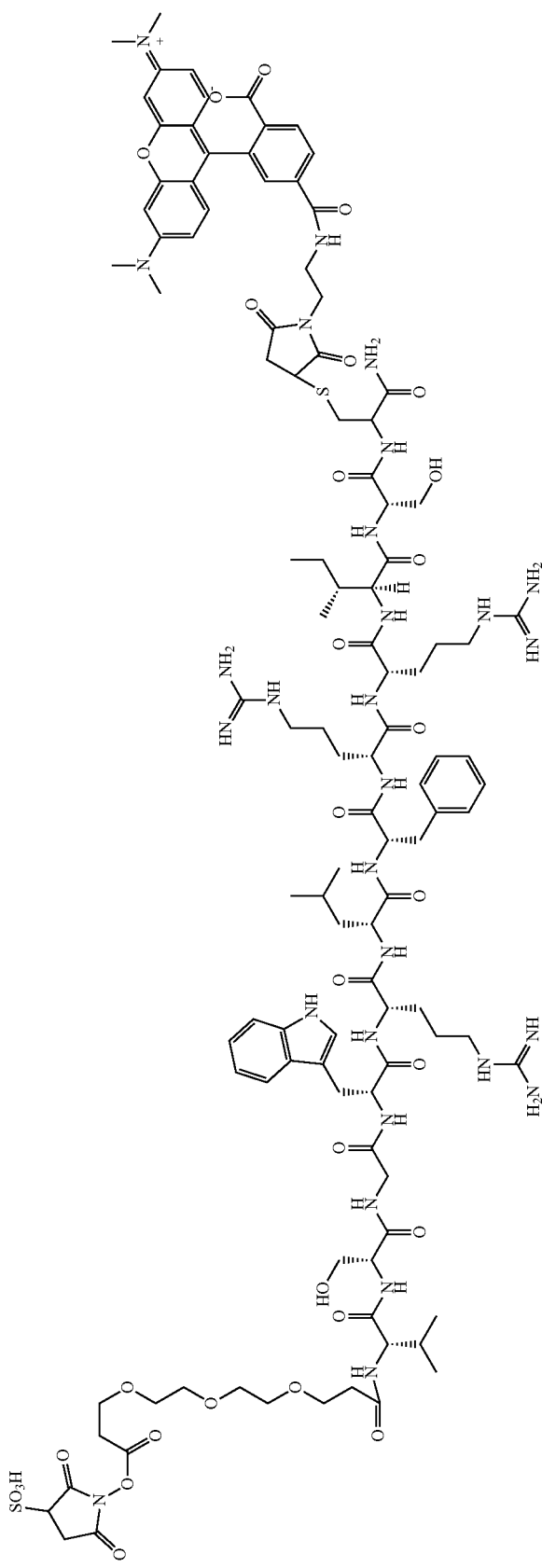

8135 was synthesized by the same method as 8136. Calculated: m/z=814.03 [M+3H]$^{3+}$; measured (ESI): m/z=814.40 [M+3H]$^{3+}$.

Example 9

SulfoSE-PEG3-SmTrip9 (939)-TAMRA (8161)

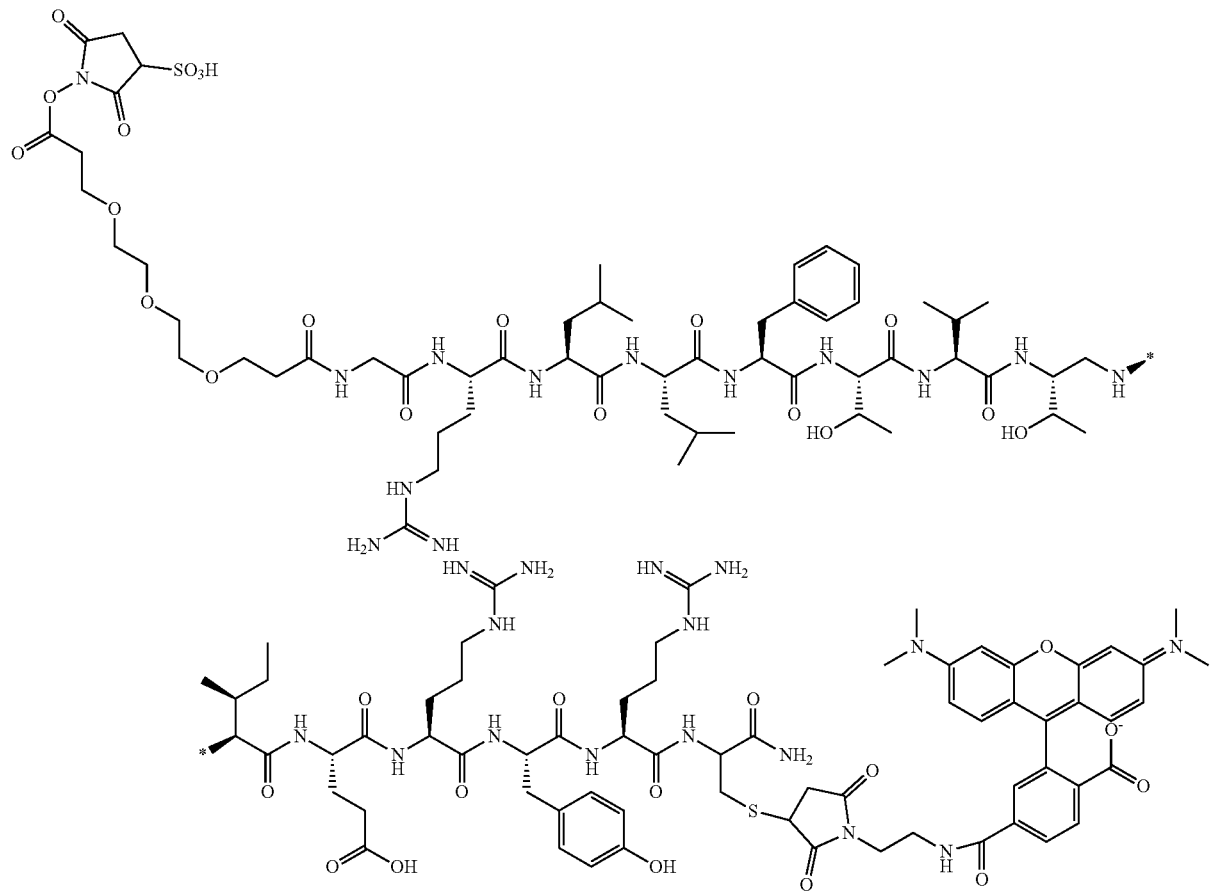

8161 was synthesized by the same method as 8136. Calculated: m/z=896.61 [M+3H]$^{3+}$; measured (ESI): m/z=897.11 [M+3H]$^{3+}$.

Example 10

Sulfo-SE-SmBiT Conjugation to an Exemplary Target Analyte

Sulfo-SE-SmBiT (7649) was dissolved in DMF at a concentration of 6 mM. A 20× molar ratio amount was added to a 1 mg/ml solution of goat anti-mouse IgG in pH 8.2 borate buffer. The reaction was mixed at room temperature for 1 hour. Unreacted sulfo-SE-SmBiT was removed by desalting column.

Example 11

Direct Immunoassay: Detection of Mouse IgG

A solution of anti-mouse IgG-sulfo-SE-SmBiT conjugate was prepared in PBS containing 10% of SuperBlock blocking agent. This was added to an equal volume of equal concentration anti-mouse IgG-HT-LgBiT conjugate also in PBS containing 10% of SuperBlock blocking agent. The mixture was dispensed into wells of a white, non-binding 96-well microtiter plate. Mouse IgG was serially diluted in PBS containing 10% of SuperBlock blocking agent and added to the wells of the plate in a volume equal to that of the anti-mouse IgG-sulfo-SE-SmBiT conjugate. The plate was placed on a platform plate shaker for 30 minutes. LCS Nano-Glo® detection reagent was added, and luminescence read. For purposes of comparison, this assay also included anti-mouse-HT-SmBit in place of the anti-mouse IgG-sulfo-SE-SmBiT conjugate.

Example 12

Indirect Immunoassay: Detection of IFNγ

IFNγ was detected using indirect immunoassay. Paired antibodies against IFNγ were used. One antibody was monoclonal antibody (mAb) while the other was biotinylated polyclonal antibody (pAb-Biotin). Paired antibodies were mixed with anti-Mouse IgG-LgBiT and Sav-SmBiT (HaloTag OR Sulfo-SE-SmBiT) to make a detection reagent. Detection reagent was added to IFNγ and incubated for 30-60 min. NanoLuc® substrate was added, and the plate read on a Glomax® luminometer.

Example 13

Competition Immunoassay: Fumonisin

A fumonisin "tracer" was prepared by combining Sav-SmBiT (HaloTag OR sulfo-SE-SmBiT) and biotinylated fumonisin to yield a fumonisin-SAv-SmBiT conjugate. This "tracer" was diluted to 1 ug/ml in PBS containing 10% SuperBlock blocking agent and added to a white, non-binding 96-well microtiter plate. Unlabeled fumonisin was serially diluted in PBS containing 10% SuperBlock blocking agent, and an equal volume was added to the wells of the plate. Anti-fumonisin-LgBiT was prepared in PBS containing 10% SuperBlock blocking agent, and an equal volume was added to the wells of the plate. The plate was placed on a platform plate shaker for 30 minutes. LCS Nano-Glo® detection reagent was added, and luminescence read.

Example 14

FcRn Binding Assay

FcRn-Avitag and Sav-SmBiT (HaloTag or Sulfo-SE-SmBiT) were mixed to make FcRn-SmBiT reagent. 25 ul of human IgG1-LgBiT tracer, 25 ul of human IgG sample, and 50 ul of FcRn-SmBiT were incubated together for 30 min at room temperature. Reagents and samples were diluted in pH6.0 PBS containing 10% superblock. NanoLuc® substrate diluted in pH 6.0 dilution buffer was added, and the plate read in a Glomax® luminometer.

Example 15

Bioluminescent Quantitation of Human Recombinant IL-6 Using NanoTrip Directly Labeled Paired Antibodies with Sulfo-SE Peptide Moieties without Built-in Linkers Experiments were conducted during development of embodiments herein to demonstrate the use of paired monoclonal antibodies that have been directly chemically conjugated with NanoTrip peptides to quantitation human IL-6. This model system consists of two monoclonal mouse antibodies that recognize IL-6 at different epitopes. Sulfo-SE-SmTrip9(824) (SEQ ID NO: 25) was chemically conjugated to one of the antibodies, and Sulfo-SE-SmTrip10(691) (SEQ ID NO: 23) was chemically conjugated to the other antibody. In the presence of IL-6, the two antibodies bind to the IL-6 thus bringing the two tags in close proximity. Addition of LgTrip (3546) (SEQ ID NO: 12) completes the complementation, and a luminescent signal is generated.

Sulfo-SE-SmTrip9(824) (SEQ ID NO: 25) and Sulfo-SE-SmTrip100(691) (SEQ ID NO: 23) were created. Anti-IL-6 mouse monoclonal antibody clone 505E9A12A3 (Thermo) was labeled with the Sulfo-SE-SmTrip100(691) (SEQ ID NO: 23) and anti-IL-6 mouse monoclonal antibody clone 5IL6 (Thermo) was labeled with the Sulfo-SE-SmTrip9 (824)-R (SEQ ID NO: 25). The unlabeled antibodies were prepped by first doing a buffer exchange into 10 mM NaHCO₃(pH 8.5) performed 2× using Zeba columns. Antibodies were then directly labeled with a 20-fold excess of the respective reactive peptide and allowed to incubate at room temperature while shaking at 1000 rpm for 2 hours. A buffer exchange was done 2× using Zeba columns to remove free linker.

A 2× stock of recombinant human IL-6 was generated in assay buffer, serially diluted 1:2 to create a dose response, and 50 ul/well added to a non-binding surface treated, 96 well solid-white plate (Costar 3600). A 2× master mix of the purified LgTrip (3546) (SEQ ID NO: 12) (final concentration 1 uM)+Sulfo-SE-SmTrip9(824) (SEQ ID NO: 25) labeled 5IL6 clone (final 10 ng/ml)+Sulfo-SE-SmTrip10 (691) SEQ ID NO: 23) labeled 505E clone (final 10 ng/ml) was created in assay buffer, and 50 ul/well added. Plates were allowed to incubate for 90 minutes prior to addition of a 5× stock of Nano-Glo® Live Cell Substrate in assay buffer, 25 ul/well added to the plate for a final concentration of 10 uM, and luminescence measured using a GloMax® Discover. Assay buffer consisted of Blocker BSA (10%) (Thermo) diluted in PBS (pH 7.0) to a final of 0.01% BSA in PBS. Samples were tested in triplicate.

Figures 10A, 10B:
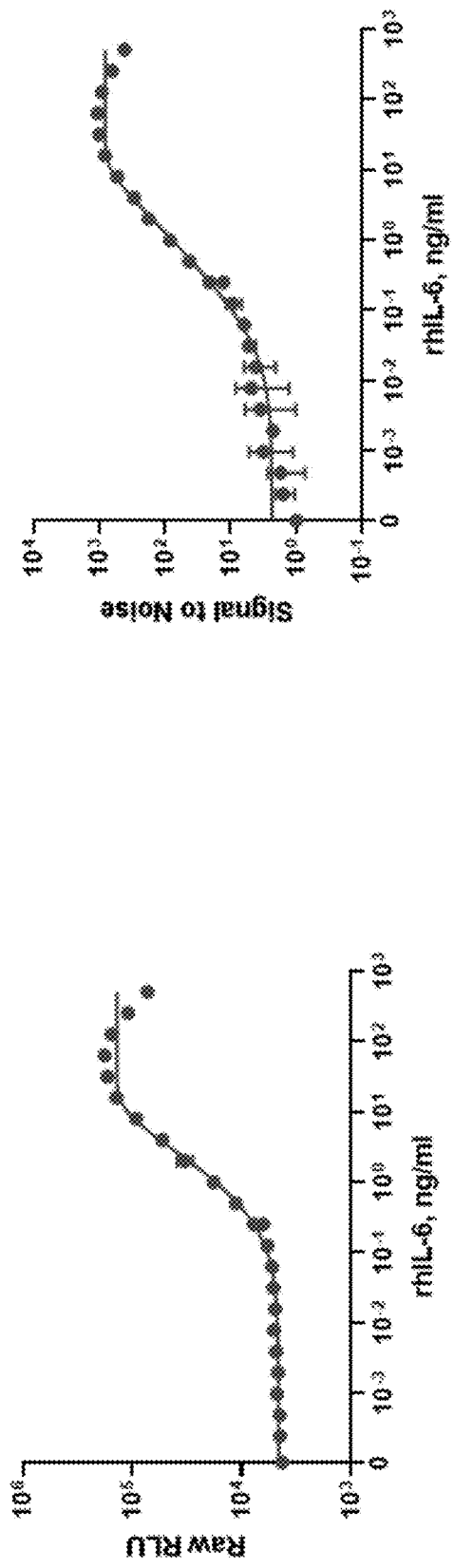
FIG. 10A-B. Graphs depicting bioluminescent quantitation of human recombinant IL-6 using Sulfo-SE-SmTrip9 (824) (SEQ ID NO: 25) and Sulfo-SE-SmTrip10 (691) (SEQ ID NO: 23) directly labeled paired monoclonal antibodies combined with LgTrip (3546) (SEQ ID NO: 12) and furimazine in a solution based homogeneous assay. A) raw RLU values and B) signal to noise calculations.

Results are depicted in FIG. 10 as raw RLU (10A) or as calculated signal to noise (10B) where signal to noise=(raw RLU−background RLU)/standard deviation of background.

Example 16

Bioluminescent Quantitation of Human Recombinant IL-6 Using NanoTrip Directly Labeled Paired Antibodies with Sulfo-SE Peptide Moieties with Built-in Linkers Experiments were conducted during development of embodiments herein to demonstrate the use of paired monoclonal antibodies that have been directly chemically conjugated with NanoTrip peptides to quantitation human IL-6. This model system consists of two monoclonal mouse antibodies that recognize IL-6 at different epitopes. Sulfo-SE-PEG3-SmTrip9(693) (SEQ ID NO: 16) or Sulfo-SE-PEG3-SmTrip9(895) (SEQ ID NO: 18) was chemically conjugated to one of the antibodies, and Sulfo-SE-PEG3-SmTrip10(691)(SEQ ID NO: 23 was chemically conjugated to the other antibody. In the presence of IL-6, the two antibodies bind to the IL-6 thus bringing the two tags in close proximity. Addition of LgTrip (3546) (SEQ ID NO: 12) completes the complementation, and a luminescent signal is generated.

Figure 14B:
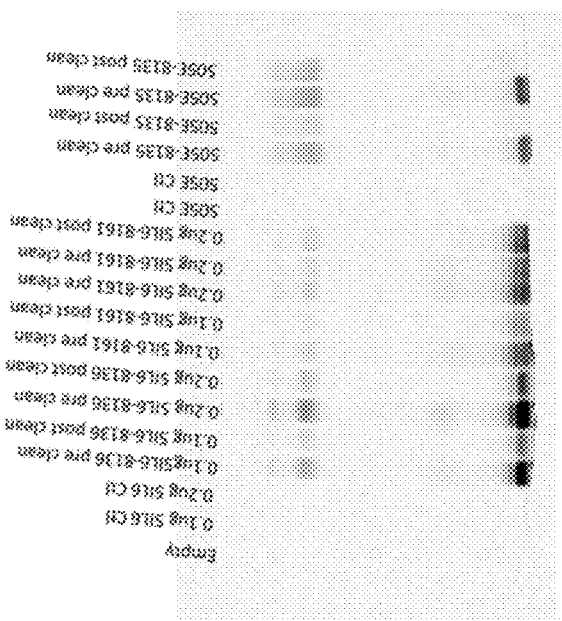
FIG. 14A-B. SDS PAGE gels of directly labeled anti-human IL-6 monoclonal antibodies. A) brightfield image capturing total protein and B) fluorescent image capturing Sulfo-SE-peptide-TAMRA (labeled antibody and excess label).
Figure 14A:
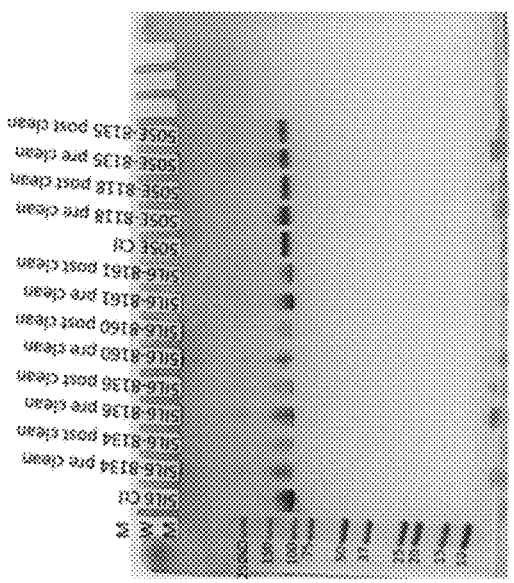
Figure 15:
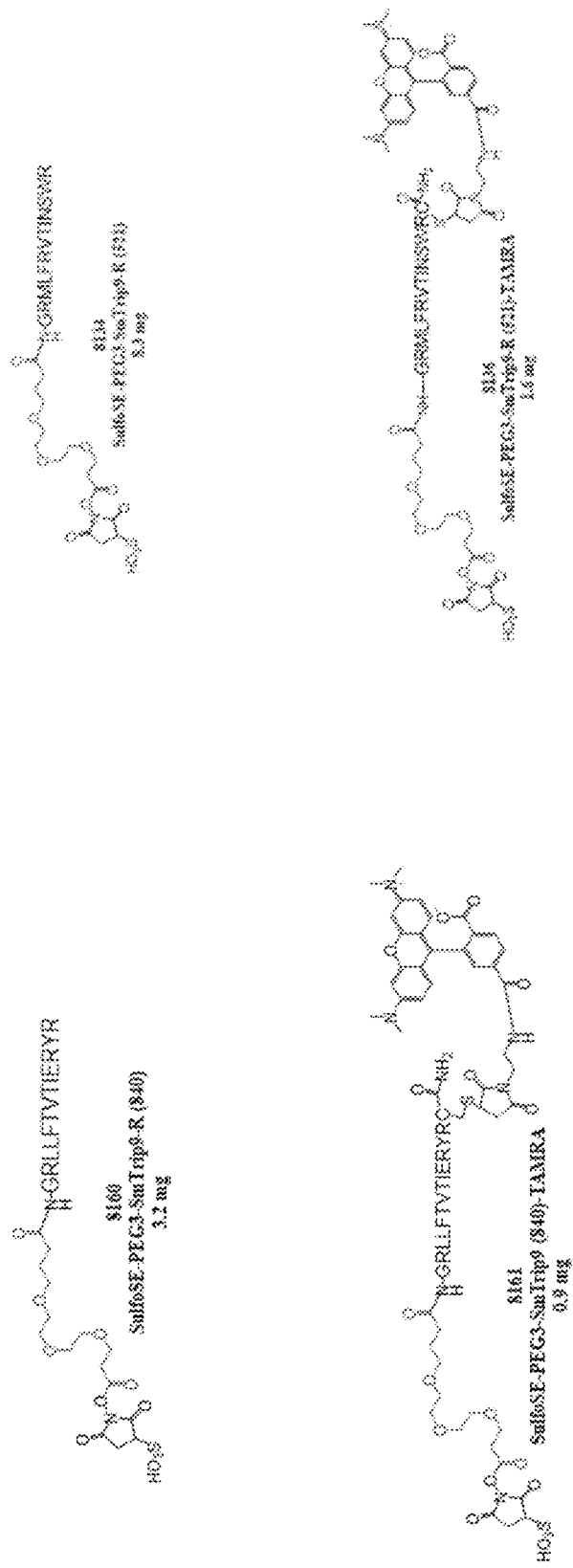
FIG. 15. Exemplary sulfo-SE peptides.

Sulfo-SE-PEG3-SmTrip9(693) (SEQ ID NO: 16), Sulfo-SE-PEG3-SmTrip9(895) (SEQ ID NO: 18) and Sulfo-SE-SmTrip100(691) (SEQ ID NO: 23) are created. Anti-IL-6 mouse monoclonal antibody clone 505E9A12A3 (Thermo) is labeled with the Sulfo-SE-PEG3-SmTrip10(691) (SEQ ID NO: 23) and anti-IL-6 mouse monoclonal antibody clone 5IL6 (Thermo) is labeled with the Sulfo-SE-SmTrip9(824) (SEQ ID NO: 25) or the Sulfo-SE-PEG3-SmTrip9(895) (SEQ ID NO: 18). The unlabeled antibodies are prepped by first doing a buffer exchange into 10 mM NaHCO₃ (pH 8.5) performed 2× using Zeba columns. Antibodies are then directly labeled with a fixed concentration of 200 uM of the respective reactive peptide and allowed to incubate at room temperature while shaking at 1000 rpm for 2 hours. A buffer exchange is done 2× using Zeba columns to remove free linker. Samples are run on an SDS PAGE total protein gel and analyzed by bright field imaging to indicate antibody labeling and determine how much excess unreacted peptide remains as shown in FIG. 14A.

A 2× stock of recombinant human IL-6 was generated in assay buffer, serially diluted 1:2 to create a dose response, and 50 ul/well added to a non-binding surface treated, 96 well solid-white plate (Costar 3600). A 2× master mix of the purified LgTrip (3546) (SEQ ID NO: 12) (final concentration 1 uM)+Sulfo-SE-PEG3-SmTrip9(693) (SEQ ID NO: 16) labeled 5IL6 clone (final 10 ng/ml) or Sulfo-SE-PEG3-SmTrip9(895) (SEQ ID NO: 18) labeled 5IL6 clone (final 10 ng/ml)+Sulfo-SEPEG3-SmTrip10 (691) (SEQ ID NO: 23) labeled 505E clone (final 10 ng/ml) was created in assay buffer, and 50 ul/well added. Plates were allowed to incubate for 90 minutes prior to addition of a 5× stock of Nano-Glo® Live Cell Substrate in assay buffer, 25 ul/well added to the plate for a final concentration of 10 uM, and luminescence measured using a GloMax® Discover. Assay buffer consisted of Blocker BSA (10%) (Thermo) diluted in PBS (pH 7.0) to a final of 0.01% BSA in PBS. Samples were tested in triplicate.

Figures 11A, 11B:
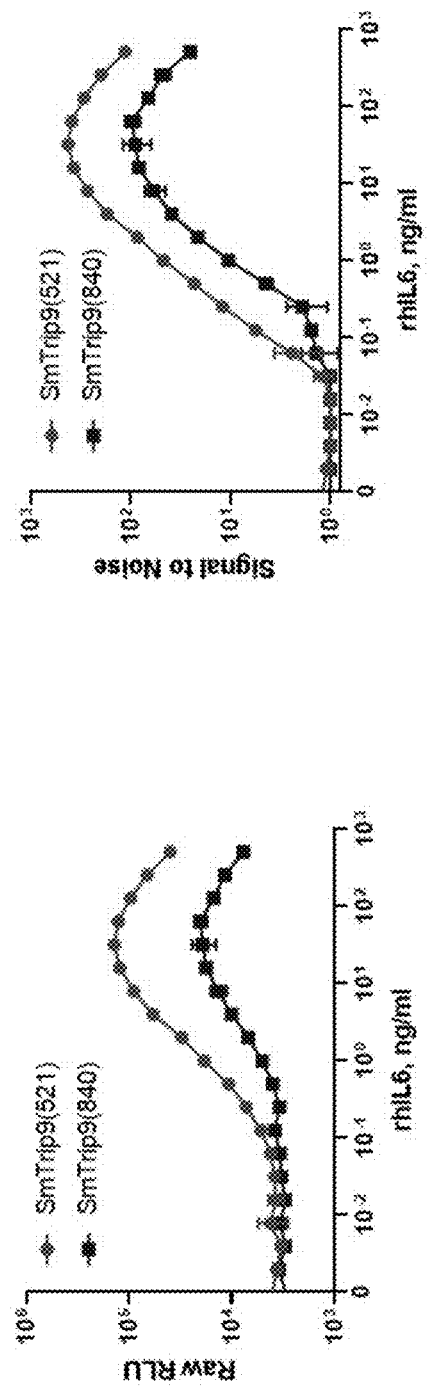
FIG. 11A-B. Graphs depicting bioluminescent quantitation of human recombinant IL-6 using Sulfo-SE-PEG3-SmTrip9 (693) (SEQ ID NO: 16) or Sulfa-SE-PEG3-SmTrip9 (840) (SEQ ID NO: 17) and Sulfo-SE-PEG3-SmTrip10 (691) (SEQ ID NO: 23) directly labeled paired monoclonal antibodies combined with LgTrip (3546) (SEQ ID NO: 12) and furimazine in a solution based homogeneous assay. A) raw RLU values and B) signal to noise calculations.
Figure 12:
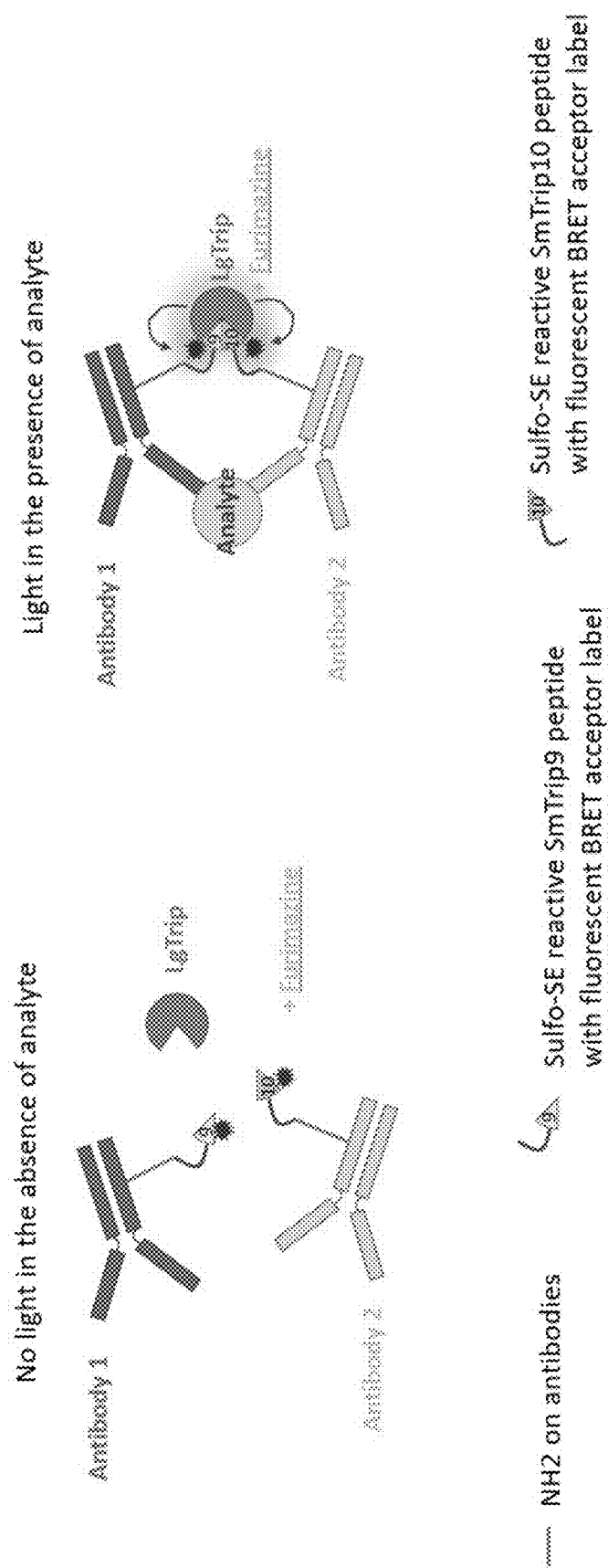
FIG. 12. Schematic illustration depicting exemplary bioluminescent resonance energy transfer (NanoBRET) immunoassay with the donor light generation resulting from complementation of the NanoTrip system using components and reagents described herein.

Results are depicted in FIG. 11 as raw RLU (11A) or as calculated signal to noise (11B) where signal to noise=(raw RLU−background RLU)/standard deviation of background.

Example 17

NanoBRET Quantitation of Human Recombinant IL-6 Using NanoTrip Directly Labeled Paired Antibodies with Sulfo-SE Peptide Moieties with Built-in Linkers Experiments were conducted during development of embodiments herein to demonstrate the use of paired monoclonal antibodies that have been directly chemically conjugated with NanoTrip peptides to quantitation human IL-6. This model system consists of two monoclonal mouse antibodies that recognize IL-6 at different epitopes. Sulfo-SE-PEG3-SmTrip9(938)-TAMRA (SEQ ID NO: 38) was chemically conjugated to one of the antibodies, and Sulfo-SE-PEG3-SmTrip10 (937)-TAMRA (SEQ ID NO: 37) was chemically conjugated to the other antibody. In the presence of IL-6, the two antibodies bind to the IL-6 thus bringing the two tags in close proximity. Addition of LgTrip (3546) (SEQ ID NO: 12) completes the complementation, and a luminescent signal is generated which in turn excites the TAMRA acceptor fluorophore allowing it to emit light at 580 nm. The donor luminescence signal and acceptor fluorophore signal are analyzed using the NanoBRET ratio of acceptor signal/donor signal is calculated.

Sulfo-SE-PEG3-SmTrip9(938)-TAMRA (SEQ ID NO: 38) and Sulfo-SE-PEG3-SmTrip10 (937)-TAMRA (SEQ ID NO: 37) were created. Anti-IL-6 mouse monoclonal antibody clone 505E9A12A3 (Thermo) was labeled with the Sulfo-SE-PEG3-SmTrip10-TAMRA (SEQ ID NO: 11) and anti-IL-6 mouse monoclonal antibody clone 5IL6 (Thermo) was labeled with the Sulfo-SE-PEG3-SmTrip9(521)-TAMRA (SEQ ID NO: 26) or the Sulfo-SE-PEG3-SmTrip9 (895) (SEQ ID NO: 18). The unlabeled antibodies were prepped by first doing a buffer exchange into 10 mM NaHCO$_3$ (pH 8.5) performed 2× using Zeba columns. Antibodies were then directly labeled with a fixed concentration of 200 uM of the respective reactive peptide and allowed to incubate at room temperature while shaking at 1000 rpm for 2 hours. A buffer exchange was done 2× using Zeba columns to remove free linker. Samples were run on an SDS PAGE total protein gel and analyzed by bright field imaging (FIG. 14A) or fluorescent imaging (FIG. 14B) to indicate antibody labeling and to determine how much excess unreacted peptide remains.

Figure 13:
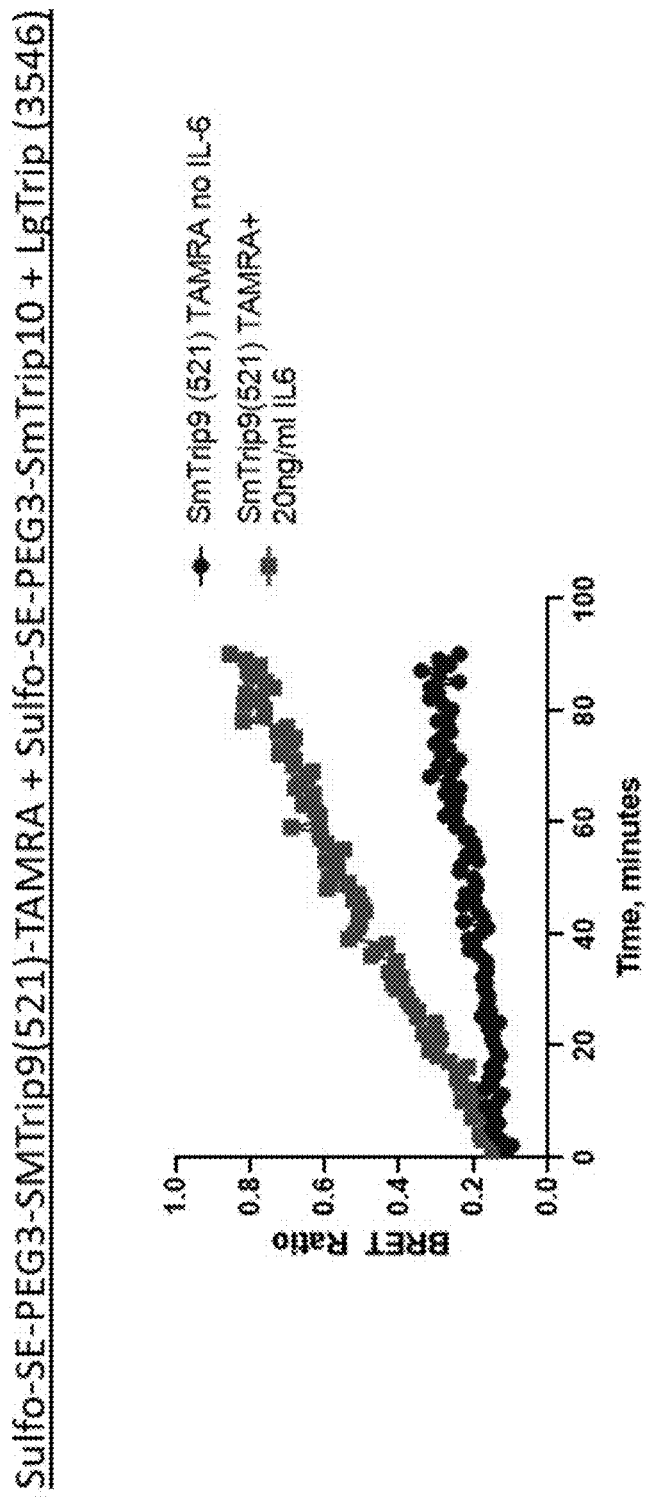
FIG. 13. Graph depicting real time binding kinetics for NanoBRET based quantitation of human recombinant IL-6 using Sulfo-SE-PEG3-SmTrip9(938)-TAMRA (SEQ ID NO: 38) and Sulfo-SE-PEG3-SmTrip10(691) (SEQ ID NO: 23) directly labeled paired monoclonal antibodies with LgTrip (3546) (SEQ ID NO: 12) and furimazine in a solution-based homogeneous assay.

A 2× stock of recombinant human IL-6 was generated in assay buffer and 50 ul/well added to a non-binding surface treated, 96 well solid-white plate (Costar 3600) (Final concentration 20 ng/ml). A 2× master mix of the purified LgTrip (3546) (SEQ ID NO: 12) (final concentration 1 uM)+Sulfo-SE-PEG3-SmTrip9(938)-TAMRA (SEQ ID NO: 38) labeled 5IL6 clone (final 10 ng/ml) 5IL6 clone (final 10 ng/ml)+ Sulfo-SE-PEG3-SmTrip10 (937)-TAMRA (SEQ ID NO: 37) labeled 505E clone (final 10 ng/ml) was created in assay buffer, and 50 ul/well added. A5× stock of Nano-Glo® Live Cell Substrate in assay buffer, 25 ul/well added to the plate for a final concentration of 10 uM, and BRET was measured using a GloMax® Discover in real time. Assay buffer consisted of Blocker BSA (10%) (Thermo) diluted in PBS (pH 7.0) to a final of 0.01% BSA in PBS. Samples were tested in triplicate. Results are depicted in FIG. 13 as raw RLU over time.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

```
SEQUENCES
WT OgLuc
                                             (SEQ ID NO: 1)
MFTLADFVGDWQQTAGYNQDQVLEQGGLSSLFQALGVSVTPIQKVVLSGE

NGLKADIHVIIPYEGLSGFQMGLIEMIFKVVYPVDDHHFKIILHYGTLVI

DGVTPNMIDYFGRPYPGIAVFDGKQITVTGTLWNGNKIYDERLINPDGSL

LFRVTINGVTGWRLCENILA

WT OgLuc Lg
                                             (SEQ ID NO: 2)
MFTLADFVGDWQQTAGYNQDQVLEQGGLSSLFQALGVSVTPIQKVVLSGE

NGLKADIHVIIPYEGLSGFQMGLIEMIFKVVYPVDDHHFKIILHYGTLVI

DGVTPNMIDYFGRPYPGIAVFDGKQITVTGTLWNGNKIYDERLINPD

WT OgLuc β9
                                             (SEQ ID NO: 3)
GSLLFRVTIN

WT OgLuc β10
                                             (SEQ ID NO: 4)
GVTGWRLCENILA

NanoLuc
                                             (SEQ ID NO: 5)
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPDGS

LLFRVTINGVTGWRLCERILA

NanoLuc Lg
                                             (SEQ ID NO: 6)
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPD

NanoLuc β9
                                             (SEQ ID NO: 7)
GSLLFRVTINV NanoLuc β10
                                             (SEQ ID NO: 8)
GVTGWRLCERILA
```

-continued

LgBiT
(SEQ ID NO: 9)
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPDGS

LLFRVTIN

SmBiT
(SEQ ID NO: 10)
VTGYRLFEEIL

HiBiT (pep86)
(SEQ ID NO: 11)
VSGWRLFKKIS

LgTrip (3546)
(SEQ ID NO: 12)
MKHHHHHHVFTLDDFVGDWEQTAAYNLDQVLEQGGVSSLLQNLAVSVTPI

MRIVRSGENALKIDIHVIIPYEGLSADQMAQIEEVFKVVYPVDDHHFKVI

LPYGTLVIDGVTPNKLNYFGRPYEGIAVFDGKKITTTGTLWNGNKIIDER

LITPD

SmTrip9
(SEQ ID NO: 13)
GSMLFRVTINS

β9/β10 dipeptide
(SEQ ID NO: 14)
GSMLFRVTINSVSGWRLFKKIS

Pep521
(SEQ ID NO: 15)
GKMLFRVTINSWK

Pep693
(SEQ ID NO: 16)
GRMLFRVTINSWR

Pep840
(SEQ ID NO: 17)
GKLLFVVVIEKYK

Pep895
(SEQ ID NO: 18)
GRLLFVVVIERYR

Pep760
(SEQ ID NO: 19)
KKMLFRVTIQKWK

Pep929
(SEQ ID NO: 20)
RRMLFRVTIQRWR

VS-HiBiT (Pep289)
(SEQ ID NO: 21)
VSVSGWRLFKKIS

Pep692
(SEQ ID NO: 22)
VSVSGWRLFRRIS

-continued

Pep691
(SEQ ID NO: 23)
VSGWRLFRRIS

Pep759
(SEQ ID NO: 24)
DKLLFTVTIEKYK

Pep824
(SEQ ID NO: 25)
DRLLFTVTIERYR

Pep521-C
(SEQ ID NO: 26)
GKMLFRVTINSWKC

Pep693-C
(SEQ ID NO: 27)
GRMLFRVTINSWRC

Pep840-C
(SEQ ID NO: 28)
GKLLFTVTIEKYKC

Pep895-C
(SEQ ID NO: 29)
GRLLFTVTIERYRC

Pep760-C
(SEQ ID NO: 30)
KKMLFRVTIQKWKC

Pep929-C
(SEQ ID NO: 31)
RRMLFRVTIQRWRC

VS-HiBiT-C (Pep289)
(SEQ ID NO: 32)
VSVSGWRLFKKISC

Pep692-C
(SEQ ID NO: 33)
VSVSGWRLFRRISC

Pep691-C
(SEQ ID NO: 34)
VSGWRLFRRISC

Pep759-C
(SEQ ID NO: 35)
DKLLFTVTIEKYKC

Pep824-C
(SEQ ID NO: 36)
DRLLFTVTIERYRC

Pep937
(SEQ ID NO: 37)
VSGWRLFRRISC

Pep938
(SEQ ID NO: 38)
GRMLFRVTINSWRC

Pep939
(SEQ ID NO: 39)
GRLLFTVTIERYRC

---

The invention claimed is:

1. A composition comprising a peptide linked to a sulfo n-hydroxysuccimidyl ester (sulfo-SE) group, wherein the peptide does not comprise a cysteine or lysine residue.

2. The composition of claim 1, wherein the sulfo-SE group is linked to the N-terminus, C-terminus, or an amino acid sidechain of the peptide.

3. The composition of claim 1, wherein the peptide comprises at least one non-alkyl amino acid selected from serine, threonine, tyrosine, glutamic acid, arginine, histidine, tryptophan and aspartic acid.

4. The composition of claim 3, wherein the at least one reactive non-alkyl amino acid is an arginine or tyrosine.

5. The composition of claim 1, wherein the sulfo-SE group is linked to the peptide by a non-peptide linker group.

6. The composition of claim 1, wherein the peptide is 4-50 amino acids in length.

7. The composition of claim 1, wherein the peptides comprise a fluorophore or chromophore conjugate.

8. The composition of claim 1, wherein the peptide is a component of a biomolecular complex.

9. The composition of claim 1, wherein the peptide comprises an amino acid sequence having 5 or fewer amino acid substitutions relative to SmBiT (SEQ ID NO: 10) SEQ ID NO: 10 (SmBiT).

10. The composition of claim 1, wherein the peptide comprises Pep691 (SEQ ID NO: 23) or SmBiT (SEQ ID NO: 10).

11. A method of labeling a biomolecule with a peptide comprising contacting the biomolecule with a composition of claim 1, under conditions such that the sulfo-SE group reacts with an amine on the biomolecule.

12. The method of claim 11, wherein the amine is a primary amine.

13. The method of claim 11, wherein the biomolecule is selected from the group consisting of an antigen, an antibody, an antibody fragment, a nanobody, a darpin, a non-antibody protein, a receptor, a ligand, a toxin, a cytokine, a nucleic acid, a nucleoprotein complex, a peptide, an amino acid, a sugar, a drug, and streptavidin.

14. A composition comprising a biomolecule labeled with a peptide of claim 1.

15. A method comprising:
(a) contacting the composition of claim 14 with an analyte, wherein the analyte is linked to a complementary polypeptide capable of forming a bioluminescent complex with the peptide on the biomolecule;
(b) contacting the bioluminescent complex with a substrate for the bioluminescent complex; and
(c) detecting luminescence.

16. The method of claim 15, wherein the analyte is selected from the group consisting of an antigen, an antibody, an antibody fragment, a nanobody, a darpin, a non-antibody protein, a receptor, a ligand, a toxin, a cytokine, a nucleic acid, a nucleoprotein complex, a peptide, an amino acid, a sugar, a drug, and streptavidin.

17. A composition comprising an analyte labeled with a peptide of claim 1.

18. A method comprising:
(a) contacting the composition of claim 17 with a biomolecule, wherein the biomolecule is linked to a complementary polypeptide capable of forming a bioluminescent complex with the peptide on the analyte;
(b) contacting the bioluminescent complex with a substrate for the bioluminescent complex; and
(c) detecting luminescence, fluorescence, and/or bioluminescence resonance energy transfer (BRET).

19. A composition comprising an analyte labeled with a first peptide linked to a first sulfo n-hydroxysuccimidyl ester (sulfo-SE) group, wherein the first peptide does not comprise a cysteine or lysine residue and a biomolecule labelled with a second peptide linked to a second sulfo n-hydroxysuccimidyl ester (sulfo-SE) group, wherein the second peptide does not comprise a cysteine or lysine residue, wherein the first and second peptides are capable of forming a bioluminescent complex in the presence of a complementary polypeptide.

20. A method comprising:
(a) contacting the analyte and biomolecule of claim 19 with the complementary polypeptide and forming the bioluminescent complex;
(b) contacting the bioluminescent complex with a substrate for the bioluminescent complex; and
(c) detecting luminescence.

21. The method of claim 20, wherein the first peptide or the second peptide is a fluorophore or chromophore-conjugated peptide and further comprising detecting fluorescence/light and/or BRET from the bioluminescent complex to the fluorophore or chromophore.

* * * * *

SEQUENCE LISTING

<160> NUMBER OF SEQ ID NOS: 39

<210> SEQ ID NO 1
<211> LENGTH: 170
<212> TYPE: PRT
<213> ORGANISM: Artificial sequence
<220> FEATURE:
<223> OTHER INFORMATION: Synthetic

<400> SEQUENCE: 1

Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45

Gly Glu Asn Gly Leu Lys Ala Asp Ile His Val Ile Ile Pro Tyr Glu
50                  55                  60

Gly Leu Ser Gly Phe Gln Met Gly Leu Ile Glu Met Ile Phe Lys Val
65                  70                  75                  80

Val Tyr Pro Val Asp Asp His His Phe Lys Ile Ile Leu His Tyr Gly
                85                  90                  95

Thr Leu Val Ile Asp Gly Val Thr Pro Asn Met Ile Asp Tyr Phe Gly
            100                 105                 110

Arg Pro Tyr Pro Gly Ile Ala Val Phe Asp Gly Lys Gln Ile Thr Val
        115                 120                 125

Thr Gly Thr Leu Trp Asn Gly Asn Lys Ile Tyr Asp Glu Arg Leu Ile
130                 135                 140

Asn Pro Asp Gly Ser Leu Leu Phe Arg Val Thr Ile Asn Gly Val Thr
145                 150                 155                 160

Gly Trp Arg Leu Cys Glu Asn Ile Leu Ala
                165                 170

<210> SEQ ID NO 2
<211> LENGTH: 147
<212> TYPE: PRT
<213> ORGANISM: Artificial sequence
<220> FEATURE:
<223> OTHER INFORMATION: Synthetic

<400> SEQUENCE: 2

Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45

Gly Glu Asn Gly Leu Lys Ala Asp Ile His Val Ile Ile Pro Tyr Glu
50                  55                  60

Gly Leu Ser Gly Phe Gln Met Gly Leu Ile Glu Met Ile Phe Lys Val
65                  70                  75                  80

Val Tyr Pro Val Asp Asp His His Phe Lys Ile Ile Leu His Tyr Gly
                85                  90                  95

Thr Leu Val Ile Asp Gly Val Thr Pro Asn Met Ile Asp Tyr Phe Gly
            100                 105                 110

Arg Pro Tyr Pro Gly Ile Ala Val Phe Asp Gly Lys Gln Ile Thr Val
        115                 120                 125

Thr Gly Thr Leu Trp Asn Gly Asn Lys Ile Tyr Asp Glu Arg Leu Ile
130                 135                 140

Asn Pro Asp
145

```
<210> SEQ ID NO 3
<211> LENGTH: 10
<212> TYPE: PRT
<213> ORGANISM: Artificial sequence
<220> FEATURE:
<223> OTHER INFORMATION: Synthetic

<400> SEQUENCE: 3

Gly Ser Leu Leu Phe Arg Val Thr Ile Asn
1               5                   10

<210> SEQ ID NO 4
<211> LENGTH: 13
<212> TYPE: PRT
<213> ORGANISM: Artificial sequence
<220> FEATURE:
<223> OTHER INFORMATION: Synthetic

<400> SEQUENCE: 4

Gly Val Thr Gly Trp Arg Leu Cys Glu Asn Ile Leu Ala
1               5                   10

<210> SEQ ID NO 5
<211> LENGTH: 171
<212> TYPE: PRT
<213> ORGANISM: Artificial sequence
<220> FEATURE:
<223> OTHER INFORMATION: Synthetic

<400> SEQUENCE: 5

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 6
<211> LENGTH: 148
<212> TYPE: PRT
<213> ORGANISM: Artificial sequence
<220> FEATURE:
<223> OTHER INFORMATION: Synthetic

<400> SEQUENCE: 6

Met Val Phe Thr Leu Glu Asp Phe Val Gly Asp Trp Arg Gln Thr Ala
```

```
                1               5                  10                 15
Gly Tyr Asn Leu Asp Gln Val Leu Glu Gln Gly Gly Val Ser Ser Leu
            20                  25                 30

Phe Gln Asn Leu Gly Val Ser Val Thr Pro Ile Gln Arg Ile Val Leu
            35                  40                 45

Ser Gly Glu Asn Gly Leu Lys Ile Asp Ile His Val Ile Ile Pro Tyr
 50                  55                 60

Glu Gly Leu Ser Gly Asp Gln Met Gly Gln Ile Glu Lys Ile Phe Lys
 65                  70                 75                  80

Val Val Tyr Pro Val Asp Asp His His Phe Lys Val Ile Leu His Tyr
                85                  90                 95

Gly Thr Leu Val Ile Asp Gly Val Thr Pro Asn Met Ile Asp Tyr Phe
            100                 105                110

Gly Arg Pro Tyr Glu Gly Ile Ala Val Phe Asp Gly Lys Lys Ile Thr
            115                 120                125

Val Thr Gly Thr Leu Trp Asn Gly Asn Lys Ile Ile Asp Glu Arg Leu
            130                 135                140

Ile Asn Pro Asp
145

<210> SEQ ID NO 7
<211> LENGTH: 11
<212> TYPE: PRT
<213> ORGANISM: Artificial sequence
<220> FEATURE:
<223> OTHER INFORMATION: Synthetic

<400> SEQUENCE: 7

Gly Ser Leu Leu Phe Arg Val Thr Ile Asn Val
1               5                  10

<210> SEQ ID NO 8
<211> LENGTH: 13
<212> TYPE: PRT
<213> ORGANISM: Artificial sequence
<220> FEATURE:
<223> OTHER INFORMATION: Synthetic

<400> SEQUENCE: 8

Gly Val Thr Gly Trp Arg Leu Cys Glu Arg Ile Leu Ala
1               5                  10

<210> SEQ ID NO 9
<211> LENGTH: 158
<212> TYPE: PRT
<213> ORGANISM: Artificial sequence
<220> FEATURE:
<223> OTHER INFORMATION: Synthetic

<400> SEQUENCE: 9

Met Val Phe Thr Leu Glu Asp Phe Val Gly Asp Trp Arg Gln Thr Ala
1               5                  10                 15

Gly Tyr Asn Leu Asp Gln Val Leu Glu Gln Gly Gly Val Ser Ser Leu
            20                  25                 30

Phe Gln Asn Leu Gly Val Ser Val Thr Pro Ile Gln Arg Ile Val Leu
            35                  40                 45

Ser Gly Glu Asn Gly Leu Lys Ile Asp Ile His Val Ile Ile Pro Tyr
 50                  55                 60

Glu Gly Leu Ser Gly Asp Gln Met Gly Gln Ile Glu Lys Ile Phe Lys
65                   70                 75                  80
```

```
Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn
145                 150                 155

<210> SEQ ID NO 10
<211> LENGTH: 11
<212> TYPE: PRT
<213> ORGANISM: Artificial sequence
<220> FEATURE:
<223> OTHER INFORMATION: Synthetic

<400> SEQUENCE: 10

Val Thr Gly Tyr Arg Leu Phe Glu Glu Ile Leu
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic

<400> SEQUENCE: 11

Val Ser Gly Trp Arg Leu Phe Lys Lys Ile Ser
1               5                   10

<210> SEQ ID NO 12
<211> LENGTH: 155
<212> TYPE: PRT
<213> ORGANISM: Artificial sequence
<220> FEATURE:
<223> OTHER INFORMATION: Synthetic

<400> SEQUENCE: 12

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp His His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Thr Thr Gly Thr Leu Trp Asn Gly Asn
    130                 135                 140
```

```
Lys Ile Ile Asp Glu Arg Leu Ile Thr Pro Asp
145                 150                 155

<210> SEQ ID NO 13
<211> LENGTH: 11
<212> TYPE: PRT
<213> ORGANISM: Artificial sequence
<220> FEATURE:
<223> OTHER INFORMATION: Synthetic

<400> SEQUENCE: 13

Gly Ser Met Leu Phe Arg Val Thr Ile Asn Ser
1               5                   10

<210> SEQ ID NO 14
<211> LENGTH: 22
<212> TYPE: PRT
<213> ORGANISM: Artificial sequence
<220> FEATURE:
<223> OTHER INFORMATION: Synthetic

<400> SEQUENCE: 14

Gly Ser Met Leu Phe Arg Val Thr Ile Asn Ser Val Ser Gly Trp Arg
1               5                   10                  15

Leu Phe Lys Lys Ile Ser
            20

<210> SEQ ID NO 15
<211> LENGTH: 13
<212> TYPE: PRT
<213> ORGANISM: Artificial sequence
<220> FEATURE:
<223> OTHER INFORMATION: Synthetic

<400> SEQUENCE: 15

Gly Lys Met Leu Phe Arg Val Thr Ile Asn Ser Trp Lys
1               5                   10

<210> SEQ ID NO 16
<211> LENGTH: 13
<212> TYPE: PRT
<213> ORGANISM: Artificial sequence
<220> FEATURE:
<223> OTHER INFORMATION: Synthetic

<400> SEQUENCE: 16

Gly Arg Met Leu Phe Arg Val Thr Ile Asn Ser Trp Arg
1               5                   10

<210> SEQ ID NO 17
<211> LENGTH: 13
<212> TYPE: PRT
<213> ORGANISM: Artificial sequence
<220> FEATURE:
<223> OTHER INFORMATION: Synthetic

<400> SEQUENCE: 17

Gly Lys Leu Leu Phe Val Val Val Ile Glu Lys Tyr Lys
1               5                   10

<210> SEQ ID NO 18
<211> LENGTH: 13
<212> TYPE: PRT
<213> ORGANISM: Artificial sequence
<220> FEATURE:
<223> OTHER INFORMATION: Synthetic
```

```
<400> SEQUENCE: 18

Gly Arg Leu Leu Phe Val Val Ile Glu Arg Tyr Arg
1               5                   10

<210> SEQ ID NO 19
<211> LENGTH: 13
<212> TYPE: PRT
<213> ORGANISM: Artificial sequence
<220> FEATURE:
<223> OTHER INFORMATION: Synthetic

<400> SEQUENCE: 19

Lys Lys Met Leu Phe Arg Val Thr Ile Gln Lys Trp Lys
1               5                   10

<210> SEQ ID NO 20
<211> LENGTH: 13
<212> TYPE: PRT
<213> ORGANISM: Artificial sequence
<220> FEATURE:
<223> OTHER INFORMATION: Synthetic

<400> SEQUENCE: 20

Arg Arg Met Leu Phe Arg Val Thr Ile Gln Arg Trp Arg
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic

<400> SEQUENCE: 21

Val Ser Val Ser Gly Trp Arg Leu Phe Lys Lys Ile Ser
1               5                   10

<210> SEQ ID NO 22
<211> LENGTH: 13
<212> TYPE: PRT
<213> ORGANISM: Artificial sequence
<220> FEATURE:
<223> OTHER INFORMATION: Synthetic

<400> SEQUENCE: 22

Val Ser Val Ser Gly Trp Arg Leu Phe Arg Arg Ile Ser
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic

<400> SEQUENCE: 23

Val Ser Gly Trp Arg Leu Phe Arg Arg Ile Ser
1               5                   10

<210> SEQ ID NO 24
<211> LENGTH: 13
<212> TYPE: PRT
<213> ORGANISM: Artificial sequence
<220> FEATURE:
<223> OTHER INFORMATION: Synthetic

<400> SEQUENCE: 24
```

```
Asp Lys Leu Leu Phe Thr Val Thr Ile Glu Lys Tyr Lys
1               5                   10
```

<210> SEQ ID NO 25
<211> LENGTH: 13
<212> TYPE: PRT
<213> ORGANISM: Artificial sequence
<220> FEATURE:
<223> OTHER INFORMATION: Synthetic

<400> SEQUENCE: 25

```
Asp Arg Leu Leu Phe Thr Val Thr Ile Glu Arg Tyr Arg
1               5                   10
```

<210> SEQ ID NO 26
<211> LENGTH: 14
<212> TYPE: PRT
<213> ORGANISM: Artificial sequence
<220> FEATURE:
<223> OTHER INFORMATION: Synthetic

<400> SEQUENCE: 26

```
Gly Lys Met Leu Phe Arg Val Thr Ile Asn Ser Trp Lys Cys
1               5                   10
```

<210> SEQ ID NO 27
<211> LENGTH: 14
<212> TYPE: PRT
<213> ORGANISM: Artificial sequence
<220> FEATURE:
<223> OTHER INFORMATION: Synthetic

<400> SEQUENCE: 27

```
Gly Arg Met Leu Phe Arg Val Thr Ile Asn Ser Trp Arg Cys
1               5                   10
```

<210> SEQ ID NO 28
<211> LENGTH: 14
<212> TYPE: PRT
<213> ORGANISM: Artificial sequence
<220> FEATURE:
<223> OTHER INFORMATION: Synthetic

<400> SEQUENCE: 28

```
Gly Lys Leu Leu Phe Thr Val Thr Ile Glu Lys Tyr Lys Cys
1               5                   10
```

<210> SEQ ID NO 29
<211> LENGTH: 14
<212> TYPE: PRT
<213> ORGANISM: Artificial sequence
<220> FEATURE:
<223> OTHER INFORMATION: Synthetic

<400> SEQUENCE: 29

```
Gly Arg Leu Leu Phe Thr Val Thr Ile Glu Arg Tyr Arg Cys
1               5                   10
```

<210> SEQ ID NO 30
<211> LENGTH: 14
<212> TYPE: PRT
<213> ORGANISM: Artificial sequence
<220> FEATURE:
<223> OTHER INFORMATION: Synthetic

<400> SEQUENCE: 30

```
Lys Lys Met Leu Phe Arg Val Thr Ile Gln Lys Trp Lys Cys
1               5                   10
```

<210> SEQ ID NO 31
<211> LENGTH: 14
<212> TYPE: PRT
<213> ORGANISM: Artificial sequence
<220> FEATURE:
<223> OTHER INFORMATION: Synthetic

<400> SEQUENCE: 31

```
Arg Arg Met Leu Phe Arg Val Thr Ile Gln Arg Trp Arg Cys
1               5                   10
```

<210> SEQ ID NO 32
<211> LENGTH: 14
<212> TYPE: PRT
<213> ORGANISM: Artificial sequence
<220> FEATURE:
<223> OTHER INFORMATION: Synthetic

<400> SEQUENCE: 32

```
Val Ser Val Ser Gly Trp Arg Leu Phe Lys Lys Ile Ser Cys
1               5                   10
```

<210> SEQ ID NO 33
<211> LENGTH: 14
<212> TYPE: PRT
<213> ORGANISM: Artificial sequence
<220> FEATURE:
<223> OTHER INFORMATION: Synthetic

<400> SEQUENCE: 33

```
Val Ser Val Ser Gly Trp Arg Leu Phe Arg Arg Ile Ser Cys
1               5                   10
```

<210> SEQ ID NO 34
<211> LENGTH: 12
<212> TYPE: PRT
<213> ORGANISM: Artificial sequence
<220> FEATURE:
<223> OTHER INFORMATION: Synthetic

<400> SEQUENCE: 34

```
Val Ser Gly Trp Arg Leu Phe Arg Arg Ile Ser Cys
1               5                   10
```

<210> SEQ ID NO 35
<211> LENGTH: 14
<212> TYPE: PRT
<213> ORGANISM: Artificial sequence
<220> FEATURE:
<223> OTHER INFORMATION: Synthetic

<400> SEQUENCE: 35

```
Asp Lys Leu Leu Phe Thr Val Thr Ile Glu Lys Tyr Lys Cys
1               5                   10
```

<210> SEQ ID NO 36
<211> LENGTH: 14
<212> TYPE: PRT
<213> ORGANISM: Artificial sequence
<220> FEATURE:
<223> OTHER INFORMATION: Synthetic

<400> SEQUENCE: 36

```
Asp Arg Leu Leu Phe Thr Val Thr Ile Glu Arg Tyr Arg Cys
```

```
<210> SEQ ID NO 37
<211> LENGTH: 12
<212> TYPE: PRT
<213> ORGANISM: Artificial sequence
<220> FEATURE:
<223> OTHER INFORMATION: Synthetic

<400> SEQUENCE: 37

Val Ser Gly Trp Arg Leu Phe Arg Arg Ile Ser Cys
1               5                   10

<210> SEQ ID NO 38
<211> LENGTH: 14
<212> TYPE: PRT
<213> ORGANISM: Artificial sequence
<220> FEATURE:
<223> OTHER INFORMATION: Synthetic

<400> SEQUENCE: 38

Gly Arg Met Leu Phe Arg Val Thr Ile Asn Ser Trp Arg Cys
1               5                   10

<210> SEQ ID NO 39
<211> LENGTH: 14
<212> TYPE: PRT
<213> ORGANISM: Artificial sequence
<220> FEATURE:
<223> OTHER INFORMATION: Synthetic

<400> SEQUENCE: 39

Gly Arg Leu Leu Phe Thr Val Thr Ile Glu Arg Tyr Arg Cys
1               5                   10
```